United States Patent [19]
Kuipers et al.

[11] Patent Number: 5,914,248
[45] Date of Patent: Jun. 22, 1999

[54] METHOD FOR CONTROLLING THE GENE EXPRESSION IN LACTIC ACID BACTERIA

[75] Inventors: Oscar Paul Kuipers, Ede; Willem Meindert De Vos, Bennekom, both of Netherlands

[73] Assignee: Stichting Nederlands Instituut Voor De Zuivelinderzoek, Netherlands

[21] Appl. No.: 08/560,007

[22] Filed: Nov. 17, 1995

[30] Foreign Application Priority Data

Nov. 18, 1994 [NL] Netherlands ............................ 9401934
Nov. 18, 1994 [NL] Netherlands ............................ 9401935

[51] Int. Cl.$^6$ ........................... C12P 21/06; C12N 15/00; C12N 1/20; C07H 21/04
[52] U.S. Cl. .................. 435/69.1; 435/252.3; 435/320.1; 435/462; 435/463; 435/465; 435/471; 536/23.2; 536/24.1
[58] Field of Search ............................... 435/69.1, 172.3, 435/252.3, 320.1, 462, 463, 465, 471; 536/23.7, 23.1, 24.1; 935/6

[56] References Cited

FOREIGN PATENT DOCUMENTS

WO 8700203  1/1987  WIPO.
WO 9204451  3/1992  WIPO.
WO 9320213  10/1993  WIPO.
WO 9400581  1/1994  WIPO.

OTHER PUBLICATIONS

Lakshmidevi et al., Molecular Characterization of Promoters of the *Lactococcus lactis* subsp. *cremoris* Temperate Bacteriophage BK5–T and Identification of a Phage Gene Implicated in the Regulation of Promoter Activity, Applied and Environmental Microbiology, vol. 56, No. 4, Apr. 1990, pp. 934–942, contents page.

Kirsch et al., The Use of B–Galactosidase Gene Fusions to Screen for Antibacterial Antibiotics, An International Journal Devoted to Research on Bioactive Microbial Products, The Journal of Antibiotics, vol. 44, No. 2, Feb. 1991, pp. 210–217, contents page.

van der Meer et al., Characterization of the *Lactococcus lactis* Nisin A Operon Genes nisP, Encoding a Subtilisin-–Like Serine Protease Involved in Precursor Processing, and nisR, Encoding a Regulatory Protein Involved in Nisin Biosynthesis, Journal of Bacteriology, vol. 175, No. 9, May 1993, pp. 2578–2588.

Shearman et al., Autolytic *Lactococcus lactis* Expressing a Lactococcal Bacteriophage Lysin Gene, Bio/Technology, vol. 10, No. 2, Feb. 1992, pp. 196–199, contents page.

Kuroda et al., Molecular Cloning and Sequencing of the Upstream Region of the Major *Bacillus subtilis* Autolysin Gene: a Modifier Protein Exhibiting Sequence Homology to the Major Autolysin and the spoIID Product, Journal of General Microbiology, vol. 138, Part 6, pp. 1067–1076.

Kuipers et al., Characterization of the Nisin Gene Cluster nisABTCIPR of *Lactococcus lactis* Requirement of Expression of the nisA and nisI Genes for Development of Immunity, European Journal of Biochemistry, vol. . 216, No. 1, Aug. 1993, pp. 281–291.

Kuipers, Oscar P. et al., "Autoregulation of Nisin Biosynthesis in *Lactococcus lactis* by Signal Transduction," J Biol Chem, Nov. 10, 1995, vol. 270, No. 45, pp. 27299–27304.

Engelke, G. et al., "Regulation of Nisin Biosynthesis and Immunity in *Lactococcus lactis* 6F3" Appl Environ Microbiol, Mar. 1994, vol. 60, No. 3, pp. 814–825.

*Primary Examiner*—Robert A. Wax
*Assistant Examiner*—Elizabeth Slobodyansky
*Attorney, Agent, or Firm*—Webb Ziesenheim Bruening Logsdon Orkin & Hanson, P.C.

[57] ABSTRACT

The present invention relates to a method for the controlled expression, in a lactic acid bacterium, of a DNA fragment containing one or more genes coding for a desired characteristic, wherein the DNA fragment is under the control of a promoter for a microbial gene which codes for an antimicrobial peptide, and the gene or genes are brought to expression on the DNA fragment by the addition of a suitable inducing factor for the transcription activation. The promoter is preferably the nisA promoter from *Lactococcus lactis*. The inducer is preferably acceptable for food products, and more preferentially is nisin or derivatives thereof. The invention also relates to a method for the production of proteins or RNA, as well as to a method for the preparation of dairy products using the expression system according to the invention. The invention finally relates to lactic acid bacteria and expression vectors for use in the method according to the invention.

22 Claims, 13 Drawing Sheets nisin Z

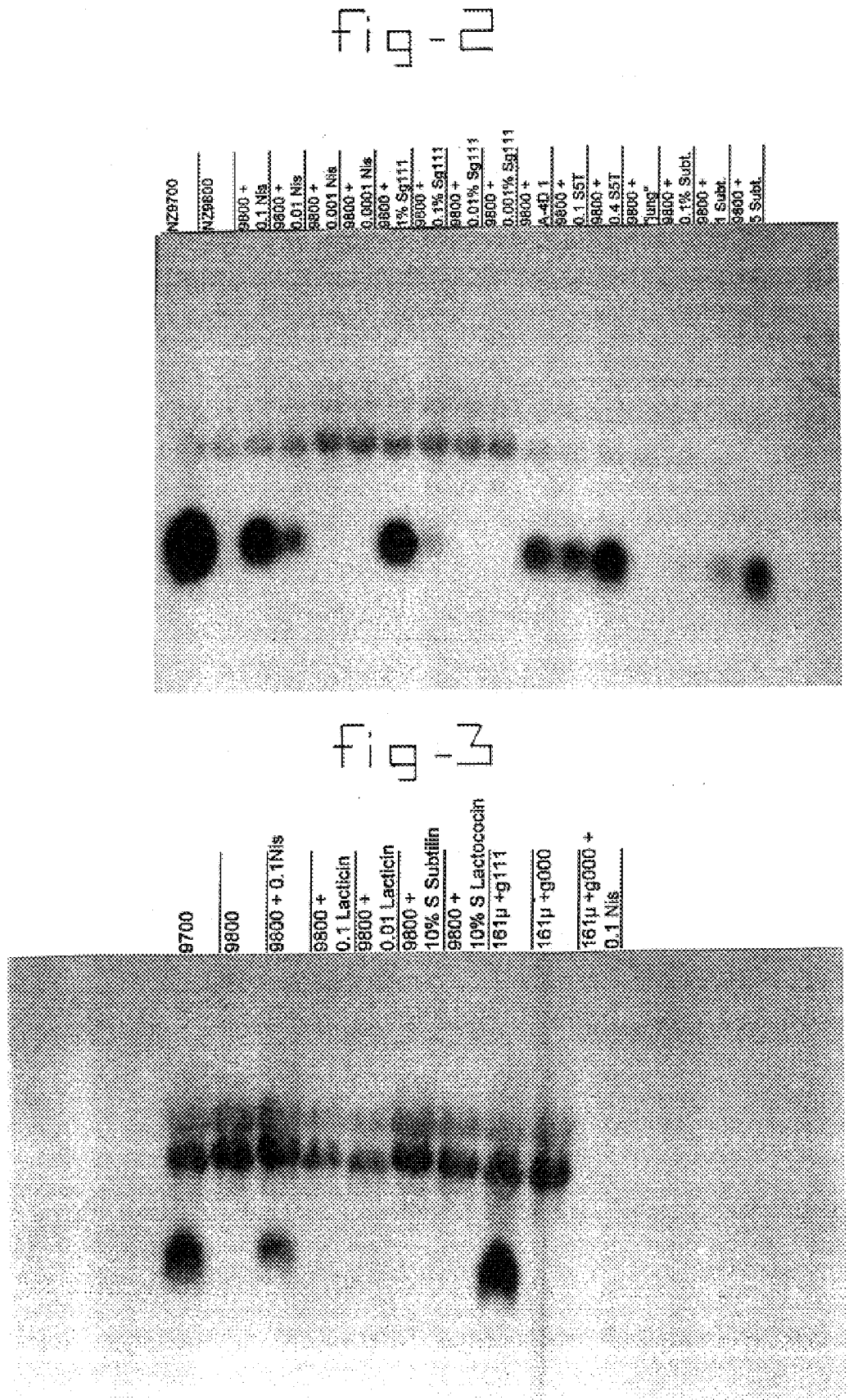

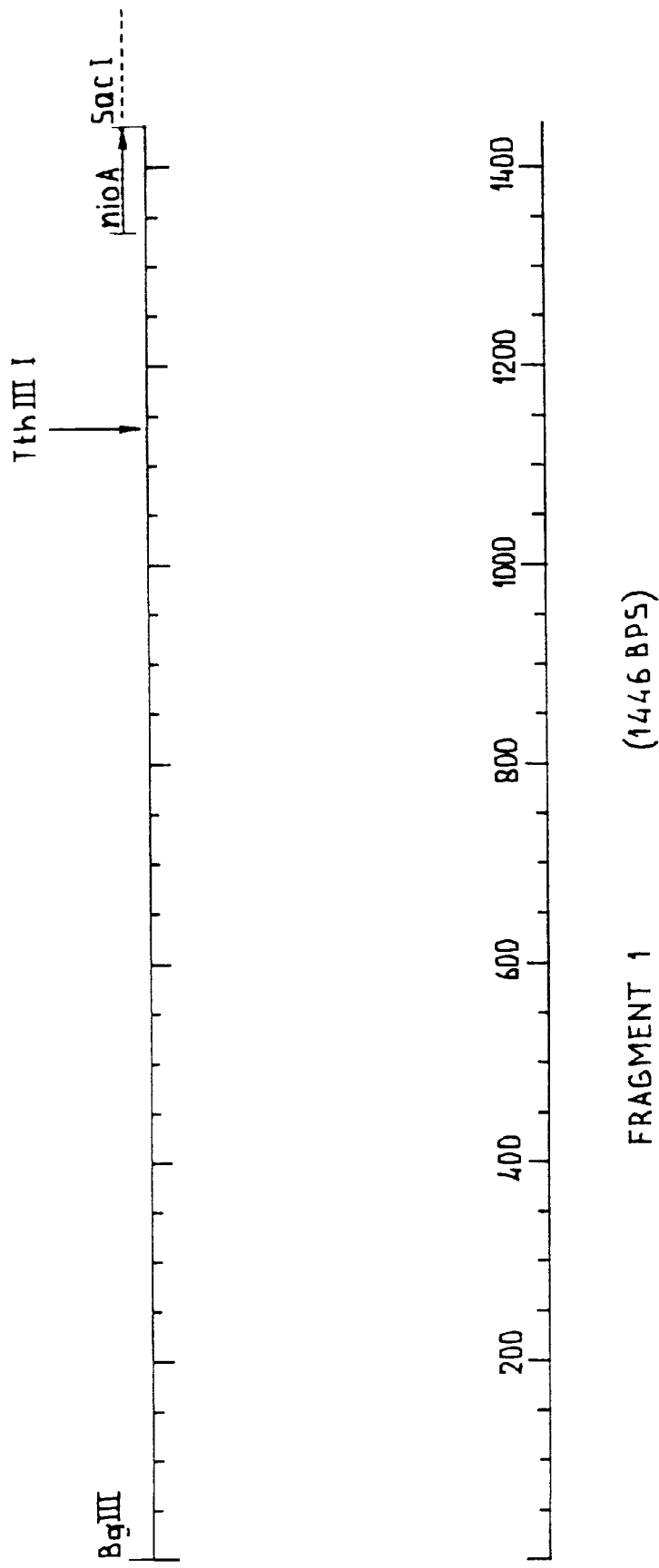

Fig-4b

NAME: FRAGMENT 1  1446 BPS DNA

SEQUENCE

```
     Bgl II
   1 AGATCTTTAA AGCAACACCT CCTAATAAAG TATGGCTGGG AGACATGACC TATATCCCTA
  61 CCAAGAAGG  TACCTTATAC TTAGCCGTGA ATATCGACGT TTTTCACGT  AAGATTGTAG
 121 GCTGGTCAAT GTCTTCACGG ATGCAAGATA AACTGGTGAG GGATTACTTC TTACAAGCTT
 181 GTGGAAAGA  ACATCCCTAG CCTGGCTTGA TTGTCCATAC TGATCAAGGG AGTCAATATA
 241 CAAGCTCTCG TTATCAATCT ACTCTTCGTC AAGTCGGTGG TCAATCTAGC ATGAGTCGTA
 301 AAGGAAATCC CTATGACAAT GCAATGATGG AGTCTTTTA  TAAGACGCTA AAGAGGAGC
 361 TTATTAATGA TGCTCATTTT GAGACAAGAG CTGAGGCTAC TCAAGAAATA TTTAAATACA
 421 TTGAGACCTA TTACAATACA AAAGGATGC  ATTCAGGTCT TGATTACAAG TCTCCAAAAG
 481 ACTTTGAAAA ATATAATTCT TAAATTCTCT TAACTCCGTG TCTAGTTTTT CGTTGACTTT
 541 CCATTATGCT TGGATTTTTT ATGTTTAAT  TCCCTTTTT  GTATACAAGC TCGTATTCTT
 601 AACAAATAAT TGGCATATCG GGTTTAAAA  TACTATGTGT TTTAAAGAAT CTCTCATGAG
 661 TTTGACGCCA ATAACTTAGA TTAAAATCAC CGTCACCTTA TTTTAGGCA  CGTTCGGCAG
 721 TAACCTTATC AAAGGTATCT CGGTCATTAA GTTTCATGAT AGTATTTACT ATTTTGACTG
 781 GTTTTGTTA  TTATCCAATC GTAAAATGA  CAAAAACAAA TAGATAAATA GATAAATATT
 841 TATGGGAGG  ACAAGTGAAC TTATCATGAT TAATTGTAAA CGATTGAGTT CTGAATGTTT
 901 CAAATTATGA GGAACAACAG AGTTGGACTA TTCTTTAAAC GCCTCGACGA TACCATCACT
 961 CTTCATTAGC CTAAAATTAA CAAGTTAAAA AATCTCTTTT AATCTAGAAT ACAAAAAATA
1021 TTTATTAAG  TTATAGTTGA CGAATATTA  ATAATTTTAT TACTTGAATG ATTTCTAGT  Tth III I
1081 TCCTGAATAA TATAGAGATA GGTTTATTGA GTCTTAGACA TACTTGAATG ACCTAGTCTT
1141 ATAACTATAC TGACAATAGA AACATTAACA AATCTAAAAC AGTCTTAATT CTATCTTGAG -35
1201 AAAGTATTGG TAATAATATT ATGTCGATA  ACGCGAGCAT AATAAACGGC TCTGATTAAA
1261 TTCTGAAGTT GTTAGATAC  AATGATTTCG TTCGAAGGAA CTACAAAATA AATTATAAGG RBS
1321 AGGCACTCAA AATGAGTACA AAGATTTTA  ACTTGGATT  GGTATCTGTT TCGAAGAAAG
1381 ATTCAGGTGC ATCACCACGC ATTACAAGTA TTTCGCTATG TACACCCCGT TGTAAAACAG
1441 GAGCTC
     SstI
     Ecl136II
          nisA
```

METHOD FOR CONTROLLING THE GENE EXPRESSION IN LACTIC ACID BACTERIA

FIELD OF THE INVENTION

The present invention relates to a method for the controlled expression, in a lactic acid bacteriaum, of a DNA fragment which contains one or more genes which code for a desired characteristic.

BACKGROUND OF THE INVENTION

Methods for the controlled expression of DNA fragments in lactic acid bacteria have already been described. However, these known Systems are not satisfactory for various reasons.

For instance, J. M. Wells et al., Appl. Environin. Microbial. 59 (1993) 3954–3959 describe a system for regulation of gene expression by an extracellular factor, in which system the heterologous T7 RNA polymerase gene is brought to controlled expression under the control of the lac promoter from the lactose operon of L. lactis. With this procedure the expression in induced by replacing glucose by lactose in the culture medium. However, this system—and comparable systems from the prior art in which the gene expression is induced by changing the sugar source in the culture medium—has a number of disadvantages, in particular in the case of large-scale preparation of, for example, foodstuffs, such as:

- The achievable degree of overexpression is restricted, usually to a factor of at most a few tens.
- The regulation is not strict/absolute, that is to say without the presence of the inducer some transcription of the regulated DNA fragment still takes place.
- The systems require the use of specific sugar sources, which can be expensive, such as, for example, xylose, which, moreover, have to be added in preponderant amounts.
- The sugar inducer can be added effectively only after removal of the sugar used beforehand.
- The presence of specific sugars in the end product is not always desirable, whilst the removal thereof—if this is even possible—is associated with additional production steps and additional costs.
- In some cases heterologous DNA must be introduced; for instance, the T7 RNA polymerase gene and promoter are used in the abovementioned system.

Lakehmidevi et al., Applied Environmental Microbiology, Apr. 1990, p. 934–942 confirm the problems which prior to the present application existed in this specialist field:

"This program of starter improvement would be enhanced by the development of procedures enabling controlled expression of specific genes. To achieve this a detailed knowledge of the regulation of gene expression in these bacteria [Lactococci] is required. [. . . .] However to our knowledge there are no published reports of detailed study on the regulation of gene expression in Lactococci."

Lakshmidevi himself describes the promoter of the bacteriophage Bk5-T which is effactive in Lactococcus. However, this is not a bacterial promoter, nor a promoter which controls the expression of an antimicrobial peptide. Moreover, the bacteriophage Bk5-T DNA is heterologous with respect to lactic acid bacteria and it is also not possible to obtain a strict/absolute regulation of the expression.

In H. Israeleen et al.: "Environmentally regulated promoters in lactococci", Abstract 16, 4th Conference on Streptococcal genetics, Santa Fé, May 15–18 (1994) various induction systems are described for L. lactis, the gene expression being controlled by changing the temperature, growth phase, oxygen concentration and/or substrate components.

A temperature-sensitive regulation of the expression of the dnaJ gene of L. lactis has also been described (J. Bacteriol. 175 [1993] 1637–1644).

International Patent Application 94/00581 (Viagen Oy) describes a Lactobacillus expression system based on the gene sequences of the surface protein (sp) gene.

However, this is not a gene that codes for an antimicrobial peptide. Furthermore, the relevant promoter or the relevant operon is not induced by its own gene product.

Moreover, it is stated on page 6, lines 20–27, that "the Lactobacillus coat protein is apparently synthesized under a wide variety of culture conditions [. . . .]. The use of this promoter provides an advantage when it is desired to increase the expressions of genes or operon of, for example, biosynthetic or degradative pathways which are otherwise tightly regulated".

The gene expression system described in said application therefore does not give a very stringent regulation, whilst the aim of the present invention is to obtain a very strict/absolute regulation.

D. Kirsch et al., Journal of Antibiotics, Part 2, No. 91, 1991, describe an assay for the detection of antibacterial antibiotics, wherein said antibiotics are added to microorganisms which contain fusions between promoters which can be initiated by antibiotics and structural genes for E. coli β-galaotosidase.

The promoters mentioned in this context are the tetA/tetR promoter of transposon Tn10 induced by tetracycline, the promoter of S. aureus erm C. erythromycin-resistance gene induced by erythromycin and the promoter of S. aureus cat 86 chloramphenicol resistance gene induced by chloramphenicol.

However, these are promoters of resistance genes; such promoters can, of course, be induced by the addition of the relevant antibiotic. However, these antibiotics are not antimicrobial peptides, nor are they the gene product of the relevant resistance genes, nor are they food-grade.

International Patent Application 87/00203 (Columbia University) describes plasmids which contain promoters for bacteriocins such as colicin. These promoters can be used to regulate the expression in E. coli. However, regulation of the expression in lactic acid bacteria using this promoter is neither described nor suggested.

Also, these promoters cannot be induced by their own gene product, that is to say colicin itself and/or derivatives thereof. According to said application, the colicin synthesis can also be induced by a large number of different factors, such as factors in the culture medium, changes in the temperature, and, for example, mitomycin C. There is therefore no question of a strict/absolute regulation.

International Patent Application 92/04451 (Genesit Oy) describes, in general terms, vectors for promoters which are effective in E. coli, B. subtilis, Lactococci and Lactobacillus, chosen from the plasmids pKHT1734 and pKHT1736 described therein.

Neither the nisA promoter, nor any other Lactococcus promoter, the induction thereof or the use thereof for Lactococci is either described or suggested in said application.

However, with these systems the degree of trancription activation is limited and the regulation is not strict, as a result of which the usability for industrial applications is limited.

Furthermore, the addition of unconventional substrate components—such as cooking salt—is undesirable in production processes in the food industry, whilst temperature induction in lactic acid bacteria with, for example, temperature-sensitive repressor systems—for sample as described for *E. coli*—is not always possible because lactic acid bacteria have a limited temperature range.

Other known systems for regulating the expression in lactic acid bacteria require inducers which are toxic and therefore not acceptable for foodstuffs, such as mitomycin C.

The systems described above also have the disadvantage that with these systems the regulation is generally negative regulation, that is to say repression of the gene expression during growth under specific conditions, which is less simple to use (more laborious) than the use of positive regulation by adding a specific substance at a desired point in time.

Furthermore, in cases where lactic acid bacteria are used in foodstuffs, such as, for example, in cheese and yoghurt, it is undesirable first to make substantial changes to the composition of the medium in order to make it is possible to regulate the transcription of a specific gene, and this is a disadvantage of all of the systems described above.

There is therefore a need for a simple method for the controlled expression of a DNA fragment coding for one or more genes in lactic acid bacteria, with which method the above-mentioned disadvantages can be overcome, so that the transcription of the one or more desired genes can be regulated positively and to a marked degree at any desired point in the growth of the lactic acid bacteria concerned, without adversely influencing the composition of the medium and thus also the desired product characteristics of the fermented product to be obtained.

This certainly also applies in cases where lactic acid bacteria are used as production organisms for foodstuffs or constituents thereof where the production has to take place in a controlled manner.

It has now been discovered that a system of this type can be obtained by making use of promoters of microbial genes which code for antimicrobial peptides from lactic acid bacteria, such as the promoter of the nisin A structural gene.

This structural gene, as well as its promoter and the sequence thereof, have already been described in the prior art [Buchman et al.; J. Biol. chem. 263 (31) (1988) 16260–16266].

International Patent Application 93/20213 (Agriculture and Food Research Council) also describes the sequence of the nisA promoter and its flanking regions, as well as plasmids which contain this promoter.

However, the said application relates to organisms and methods for the production of variant nisins, including nisin Z, which in general are produced by mutating and/or completely inactivating the nisA structural gene.

However, the expression of these mutated nisin structural genes is preferably carried out under the influence of a lacA promoter; to this and the naturally occurring nisin promoter is replaced by said heterologous promoter.

However, the problem addressed by the present application, that is to say the provision of a preferably homologous expression system in Lactococcus, which is able to give a strict/absolute regulation of the gene expression using (in low concentrations) suitable inducers, which preferably are acceptable for food products, is not solved by the said application.

This is also apparent from a discussion of International Patent Application 93/20213 by one of its inventors, M. J. Gasson, in FEMS Microbiol. Rev. 12 (1993), 3–20, in which it is stated that "while the lactose operon is subjected to negative regulation it is only partially switched off during repression. more effective genetic switches are desirable [. . .]".

J. R. van der Meer, O. P. Kuipers, W. M. de Vos et al., Journal of Bacteriology, May 1993, p. 2578–2588 describe the nisP and nisR genes of *L. lactis*. In this article it is stated that the nisR gone product is a "protein regulatory involved in nisin biosynthesis".

However, the nisR gene product is not a protein with antibacterial activity but a factor which—together with the nisK gene product—is involved in the signal transduction of extracellular nisin, which results in transcription activation. Moreover, although the nisR gene does contain a promoter, this promoter in not induced by the nisR gene product, nor by nisin or its derivatives. Moreover, the nisA and nisZ promoters cannot be induced by the nisR gene product.

It has now been discovered that promoters which code for antimicrobial peptides, and in particular the nisA promoter and the nisZ promoter, can be induced by their own gene product, that is to say the antimicrobial peptide for which they regulate the expression in nature, and/or derivatives thereof. Thus, it has ben found that the nisA promoter can be induced Strictly/absolutely by nisin or suitable analogues/derivatives thereof, for example derivatives obtained after post-translational expression, By this means it is possible, by adding such an inducer/inducing factor in a controlled manner at a desired point in time, to obtain expression of a homologous or heterologous gene which is operably connected to said antimicrobial promoters.

SUMMARY OF THE INVENTION

The present invention therefore relates to a method of the type described above, characterised in that
the DNA fragpent is under the control of a promoter of a microbial gene which codes for an antimicrobial paptide, and
the genes coded for on the DNA fragment are brought to expression by the addition of a suitable inducer for the transcription activation.

DETAILED DESCRIPTION OF THE INVENTION

The promoter is generally selected from promoters of genes which code for antimicrobial peptides, such as, for example, the lantibiotios, and examples of such genes will be apparent to those skilled in the art.

Furthemore, a person skilled in the art will be able, on the basis of the description given below, to determine which promoters are suitable for use in the present invention, and which inducing factors must or can be used with these promoters.

The promoter used is preferably derived from lactic acid bacteria, more particularly from the species or strain which is used for bringing the desired DNA fragment to expression, so that the promoter is homologous with respect to said expression host.

A non-limiting example of a promoter according to the present invention, which is also preferred, is the promoter of the nisA gene or the nisZ gene from Lactococcus lactis.

The inducer used can be any compound which induces the gene expression. The inducing factor employed depends on the promoter used and a person skilled in the art will be able to determine, on the basis of the description given below, which inducing factor is suitable for the promoter used.

The preferred inducers—such as nisin and derivatives thereof—are advantageously acceptable for foodstuffs, more particularly for dairy products, so that the method according to the invention can be employed in the preparation of these products. The inducers used also offer a substantial advantage in the production of pharmaceuticals by lactic acid bacteria, because they are not toxic and consequently offer a relatively inexpensive option for a safe production method for these substances.

Usually, and preferably, the inducer will be an antimicrobial peptide or a suitable derivative, analogon, mutant, fragment and/or variant thereof, the inducer activity of which is sufficient to give induction. The latter inducers can be obtained, for example, by post-translational modification in vivo, or by preparing a derivative in a manner known per se, for example enzymatically or via a chemical route.

Furthermore, the inducer used will usually be derived from the gene product of the (structural) gene which in the wild type is under the control of the promoter used. For instance, the nisA or nisZ promoter preferably used can be induced by derivatives of nisin, which are preferably chosen from nisin A, nisin Z and/or analogues, mutants, variants and/or derivatives thereof.

The inducers are preferably produced in and by a lactic acid bacterium, so that said inducers are not alien to the lactic acid bacterium use and/or the production process used.

This also makes it possible simply to add the inducer in the form of (a supernatant of) a culture of a lactic acid bacterium which produces this inducer, which offers appreciable advantages from the standpoint of process engineering.

The inducer used is therefore acceptable for foodstuffs, relatively inexpensive, simple to produce and easy to add, without having an adverse effect on the culture medium or the end product.

However, the invention is not restricted to the abovementioned preferred inducers, but comprises, in general, the use of all factors which are able to induce the expression in a suitable manner.

The present invention in based on the fact that certain promoters of genes, especially of gene clusters, which code for antimicrobial peptides can be regulated externally in a simple manner, in particular by adding their gene product—optionally after further post-translational modifications—or a suitable derivative, analogon, mutant, fragment and/or variant thereof.

This is surprising, because the antimicrobially active inducer gives induction at levels which are far below the MIC value, the minimum inhibitory concentration (De Vos et al. (1993) Appl. Environm. Microbiol. 59, 213–218) for the micro-organims used.

The invention therefore comprises, in the broadest terms, the culture of a lactic acid bacterium which contains a desired gene under the control of a promoter as described above. The culture of said lactic acid bacterium can be carried out in the conventional manner, in conventional culture media and using the conventional medium components.

Usually and preferably, milk, milk-containing and/or milk derived media are used. It should be noted that in general, such media contain all the substances required for the growth of the lactic acid bacteria, so that further medium components to facilitate growth of the lactic acid bacteia is not necessary, although this is included within the scope of the invention.

The induction of the expression of the desired gene can then be obtained by positive regulation, that is to say by adding the inducer to the culture described above.

The addition of said inducer can be carried out at any desired point in time during the culture and particularly at the point in time when expression of the gene is desirable.

Furthermore, advantageously only very small amounts—i.e. less than 1 $\mu$g/l—of the inducing factor will be required. Thus, in the case of the nisA promoter, it is sufficient to add the inducing nisin derivatives in an amount of 0.000001–10 mg/l, preferably 0.00001–0.1 mg/l, based on the total volume of the culture, for example in the form of a small amount of a fermentation fluid of a nisin-forming *L. lactis* strain.

The DNA fragment with the one or more desired genes can be brought under the control of the promoter by any means known per se, and suitable techniques will be apparent to persons skilled in the art and/or will be described in more detail below and in the abovementioned prior art, incorporated herein by reference.

In general, this comprises operably linking a nucleotide sequence coding for the one or more genes to be expressed to a nucleotide sequence coding for the promoter, the term "operably linked" having the usual meaning in the art, i.e. that the nucleotide sequences are in the correct reading frame with respect to each other, or possess their own binding sites, so as to enable translation and optionally polycistronio transcription (when the genes code for functional proteins or polypeptides) of the genes under the control of the promoter. (All other terms used in the present description, when not specifically defined herein, have the general meaning as known in the art).

In order to operably link these nucleotide sequences, the nucleotide sequence of the structural gene can be inserted into the DNA material on which the promoter is present and/or naturally occurs, optionally after inactivation, mutation or deletion of the gene naturally controlled by said promoter, the nucleotide sequence coding for the promoter can be inserted into the DNA material carrying the structural gene to be expressed, i.e. in front of the structural gene, or the nucleotide sequence coding for the promoter and the nucleotide sequence coding for the structural gene can be linked to form a new DNA material for instance an expression cassette maintained an a plasmid. With all these techniques, the nucleotide sequence coding for the promoter and/or the nucleotide sequence coding for the structural gene(s) can be identified, isolated and optionally transferred, inserted and/or linked by means of conventional genetic manipulation and cloning techniques as for instance described in the prior art, mentioned herein, which is incorporated by reference.

Furthermore, any desired DNA fragment which codes for a desired characteristic, a desired protein, enzyme or peptide, or a desired ribonucleic acid can be brought to controlled expression by the method of the invention.

When the structural gene to be expressed codes for a protein or polypeptide, this peptide can also be a precursor of the mature polypeptide, such as a pre, pro or prepro form thereof, which can undergo further post-translational modifications. As such, the invention comprises both expression of the mature protein as well as expression of these "ripening forms", with or without further post-translational modifications depending upon whether the expression host contains the cellular and enzymatical mechanisms to carry out said modifications.

The invention further comprises both secretion of the form polypeptide or protein (in mature and/or ripening form), i.e. by crossing the bacterial cell wall and/or cell envelope. The invention also comprises intracellular accumulation of the desired polypeptide or protein (in mature or ripening form), optionally followed by disruption of the cell wall so as to free said protein or polypeptide into the medium, i.e. by lysis or by the use of holines as described herein below.

The invention also comprises the expression of in-frame fusions of the desired protein/polypeptide, and the protein naturally controlled by the promoter, under the control of said promoter. After that, the desired protein or polypeptide can be obtained by cleavage of said fusion in a manner known per se.

In the method according to the invention, genes on said DNA fragment are preferably brought to increased expression. In this context it is generally possible to obtain an increase in the expression by a factor of more than 100, which is appreciably more than the expression ratio which can be obtained using systems from the prior art. Furthermore, in the absence of the inducing factor, a very low level of transcription for the desired gene is obtained.

The increased expression, in combination with the very strict regulation, makes the method according to the present invention particularly suitable for the overproduction of gene products at a specific point in the growth of lactic acid bacteria, and methods of this type constitute a further aspect of the invention.

The method of the invention therefore makes it possible to obtain efficient expression of desired homologous or heterologous genes in lactic acid bacteria by positive regulation of the transcription of said genes. Said regulation can be obtained by the addition of a component of a naturally occurring fermentation product, which can be added at various points in time without it being necessary first to make other modifications to the composition of the medium.

All these factors contribute to the very wide applicability of the method according to the invention, so that the present application meets a need which has already existed for a long time and thus constitutes an important step forward in the application of regulatory gene expression systems. Further advantages of the present invention will become apparent from the description given below.

The method according to the present invention is in particular suitable for use in the preparation of proteins and/or RNA in lactic acid bacteria and methods of this type constitute a further aspect of the invention.

In this context, the method according to the invention makes it possible, in particular, to separate the growth of the production organism from the production of the desired RNA or protein. This can be very useful in the optimisation of product production on a large scale.

The method according to the present invention can be used for the preparation of proteins such as enzymes, membrane proteins, lytic proteins, extracellular proteins, antimicrobial proteins, and the like.

Thus, according to a particular aspect, the method of the invention is very suitable for the overproduction of antimicrobial peptides, such as nisin A, nisin Z and/or derivatives or mutants thereof, by bringing coding structural genes onto a plasmid under the control of the promoter fragment described. Said overproduction can be carried out using a wild type lactic acid bacterium with a conventional nisin promoter, such as that of nisA, and induction with nisin or a derivative thereof.

The familiarity with the inducer is of great importance for increasing the production of antimicrobial paptides, and methods for this constitute a further aspect of the invention. This can take place, for example, by achieving a sufficiently high concentration of the inducer, for example by addition, under various fermentation conditions, such as batch culture, continuous culture, or production by immobilised cells. In addition, it is possible to guarantee a sufficient degree of induction by, for example, immobilisation of the inducer.

Other desired protains and/or gene products can be obtained by operably placing genes coding for the product of interest in the chromosome of the microorganism downstream of the promoter with the aid of well-known chromosomal integration techniques (see, for example, Leenhouts, K. J., Kok, J. and Venema, G. (1991) *J. Bact.*, 173, 4794–4798 and Kuipers, O. P., Beerthuyzen, M. M., Siezen, R. J. and de Vos, W. M. Eur. *J. Biochem.*, 216 (1993), 281–291, and Sambrook et al also raferred to as Maniati et al- olecular cloning, A Laboratory Manual, Second edition, Cold Spring Harbor Press, 1989, the contents of which are incorporated here by reference), or by cloning the said genes in expression vectors such as plasmids on which the relevant promoter fragment is present, and then bringing said genes to expression in a lactic acid bacterium.

The method according to the present invention can, moreover, advantageously be used for the production, in a regulated manner, of RNA molecules which are active as "anti-sense RNA" with respect to a gene to be inactivated, so that specific genes can be inactivated. The possibility of the use of antisense RNA in lactic acid bacteria has already been described in the prior art, but was restricted by the absence of usable induction systems (see, for example, S. G. Kim and C. A. Batt, Appl. Environm. 57 (1991), 1109–1113.)

Furthermore, the method according to the invention can be used for the production of RNA or proteins which have a negative effect on the growth of the lactic acid bacterium used, such as lytic enzymes and other gene products which are intrinsically lethal.

According to this aspect of the invention, controlled lysis of lactic acid bacteria can be achieved, for example so as to be able to induce and to control the release of intracellular enzymes—which according to the method of the invention can be produced intracellularly—in the final fermented product. This offers great advantages for the production and accelerated maturing of various fermented foodstuffs, such as, for example, cheese and yoghurt.

An advantage in this context is, in particular, that the controlled lysis can be induced at any desired point in time during culture by the addition of the inducer, said inducer preferably being acceptable for foodstuffs.

It will be clear that such methods could not, or could hardly, be achieved with systems from the prior art because these known systems were not able to produce the strict/absolute regulation required for this purpose or were not acceptable for use in the preparation of foodstuffs.

For instance, M. J. Gasson, FEMS Microbiol. Rev. 12 (1993) 3–20, describes a system in which a Listeria bacteriophage lysine is brought to expression in *L. lactis* under the control of a lac promoter, in which context it is stated that:

"While the lactose operon is subject to negative regulation it is only partially switched off during repression. More effective genetic switches are desirable [. . .]".

With the method according to the present invention a virtually absolute positive regulation is obtained, which makes it possible to bring the lysines or other genes to expression highly selectively.

In a further aspect, the invention therefore relates to methods for the preparation of foodstuffs, in particular dairy products, in which the expression system according to the present invention is used. The preparation of these food products using the invention can be carried out analogously to known methods, for example by using a lactic acid bacterium with an expression system according to the invention, and induction of the expression by the addition of a suitable medium component which is safe in food.

It will be clear to a man skilled in the art that in the production of dairy products, the culture medium will be milk or a milk derived or milk containing medium, which is usually used for the production of the relevant dairy product.

Finally, the invention relates to a lactic acid bacterium which contains one or more homologous or heterologous genes, which have been brought under the control of a promoter of a microbial gene (cluster) which codes for an antimicrobial peptide, and which differ from the genes which are naturally—i.e. in the native form or the wild type—regulated by this promoter.

According to a specific embodiment, the promoter in this procedure is the promoter of the nisA or nisZ gone of *L. lactis* and the homologous and heterologous gene does not belong to the nisin gene cluster described below.

The one or more genes can be introduced into the chromosomal DNA of the microorganism or by means of a suitable vector, such as a plasmid, in accordance with techniques which are known per se and are described below.

In a further aspect, the invention therefore relates to a transformation vector, containing promoter of a microbial gene, which codes for an antimicrobial peptide, and one or more genes which are brought under the control of this promoter and which differ from the genes which naturally—i.e. in the native form or in the wild type of the relevant microorganism from which the promoter originates—are regulated by this promoter. The transformation vector is preferably a plasmid, but other suitable transformation vectors, such as transposons, phages and the like, can also be used and can be obtained by methods known to those skilled in the art.

The transformation vector can also be an expression vector, such as a plasmid, in which the one or more genes on the vector are expressed under the control of the promoter present on the vector.

The use of such expression vectors offers a very simple way of expressing heterologous structural genes in lactic acid bacteria, to transfer and/or incorporate a desired haterologous promoter into lactic acid bacteria, and/or both.

Therefore the promoter and the gene(s) controlled by it can be expressed from a suitable expression vector, or after incorporation of their sequences into the host's DNA.

On example of a microorganism of the invention is the lactic acid bacterium *L. lactis* NZ 9800+pNZ 8008, which was filed with the Centraal Bureau Schimmeloultures (CBS; Central Bureau of Mold Cultures) in Baarn on Nov. 16, 1994 under number CBS 563.94. This microorganism contains the plasmid PNZ 8008 according to the invention, comprising the gusA gene under the control of the nisA promoter of *L. lactis*.

Finally, the invention relates to the use of a lactic acid bacterium as described above in the above method(s) according to the invention.

However, the applicability of the invention is not restricted to lactic acid bacteria. Other microorganisms, in particular Gram-positive bacteria such as *B. subtilis*, can also be used in an analogous manner, as will be apparent to those skilled in the art.

The present invention is, however, of particular advantage in the preparation of foodstuffs with the aid of lactic acid bacteria.

The invention is explained in more detail below by means of a preferred embodiment, in which the promoter of the nisA gene from *L. lactis* is used. As already stated above, the invention is not restricted to this specific promoter.

The method according to the said preferred aspect of the present invention offers a possibility for activating the transcription of any desired gene which is placed under the control of a specific promoter fragment. In this context, use is made of a fragment containing nisA promoter which can be smaller than 320 bp, with a naturally occurring antimicrobial peptide as inducer.

In this context it has been found that the inducer for transcription activation of the nisA gene in *L. lactis* strains is the completely modified and proteolytically activated gene product of nisA or nisZ: nisin A or nisin Z (and derivatives thereof), and that this can be used as much as inducer in very low concentrations (less than 10 ng/ml).

This is surprising, partly because of the fact that to date it was known only that autoregulation can occur through the own gene product, but not that, for this purpose, post-translational modifications have to take place on this gene product before the inducing characteristic is produced. The unmodified gene product is not capable of playing the inducing role. This form of autoregulation for the production of antimicrobial peptides, in particular those which are produced by lactic acid bacteria, is a surprising and novel phenomenon.

Furthermore, neither in the case of research on subtilin—or of research on nisin—have there ever previously been indications of the need for the presence of a specific medium component in connection with regulation of gene expression of the structural gene or of other genes located in the gene cluster.

The nisA promoter preferaly used—like the nisZ promoter which is also suitable—forms part of the gene cluster of *L. lactis* which is responsible for the production of nisin, a well-charactesrised antimicrobial peptide which is produced by various strains of the lactic acid bacterium *L. lactis* and is used in the food industry as a natural preservative because it inhibits the growth of undesirable Gram-positive bacteria (see Kuipers et al., ECB6: Proceedings of the 6th European congress on Biotechnology, Elsevier Science, 1994).

Nisin belongs to the group of antimicrobial peptides which are referred to as 'lantibiotics'. Molecules of this type are characterised by a low molecular mass (<4 kDa), by the presence of unsaturated amino acid residues, such as dehydroalanine and dehydrobutyrine and by the thioether bridges of lanthionine residues, which are produced by the addition of the sufhydryl group of cysteines to the double bond of the above-mentioned unsaturated amino acids.

It is assumed that post-translational modifications of the ribosomal synthesised precursor peptide of 57 amino acids, which has no antimicrobial activity, take place, followed by secretion and the removal of the leader peptide, which leads to the active nisin in the medium.

To date, 8 genes, for which the nucleotide type sequence has been determined, which are involved in the biosynthesis, secretion, regulation and immunity of nisin have been identified. These genes are located on an approximately 12 kb fragment of the nisin/sucrose transposon Tn5276 or Tn5278 or Tn5301, and are named successively nisABTCIPRK or nisZBTCIPRK. The function of these genes in the nisin biosynthesis is only partly knowm. The structural gene nisA, and also the naturally occurring variant thereof, nisZ, code the unmodified precursor peptide of nicin which consists of 57 amino acid residues. The promoter sequence of the structural gene and the transcription start have been identified and a clear transcript of approximately 260 bp can be demonstrated after Northern blotting, see Kuipers, O. P., Beerthuyzen, M. M., Siezen, R. J., and de Vos. W. M., *Eur. J. Biochem.* 216 (1993), 281–291, the contents of which are incorporated here by reference. However, this article gives no information on the induction of this promoter.

It has been demonstrated that transcription of the nisA gene is dependent on the integrity of nisA itself, because a 4 bp deletion in the middle of the nisa gene leads to a complete absence of transcription of this truncated ΔnisA, see Kuipers, O. P., Beerthuyzan, M. M., Siezen, R. J., and de Vos. W. M., *Eur. J. Biochem.* 216 (1993), 281–291, the contents of which are incorporated here by reference.

It is also known that the presence of an intact nisR is in all cases required for expression of nisA. On the basis of the existing homologies between nisK and nisR with well-characterised regulator genes belonging to the family of two-component regulator genes, it can be assumed that the nisK gene product (probably a histidine kinase) acts as sensor for a factor which has been unknown hitherto and that the latter activates the nisR gene product via a phosphorylation reaction, as a result of which transcription activation of the nisA gene takes place. It is therefore assumed that nisR and nisK are involved in the expression by the nisA promoter and play a role in the signal transduction under the influence of an extra-cellular inducing factor present.

However, the invention is not restricted to this or another explanation.

Also, although the invention is not limited thereto, applicant has found some indication that nisin producing cells in vivo stop producing nisin once they have reached the stationary phase, or at least that the amount of nisin produced is greatly reduced. Therefore, it is assumed for the preferred promoters of the nisin gencluster of the invention that transcription/expression of the gene(s) controlled by said promoters will for the most part take place during logaritmic growth, although the invention is not limited to any particlar growth phase of the expression host, and transcription/expression during for instance the stationary phase is explicitly included.

Also, although the promoters of the invention provide for a strict/absolute regulation of gene expression, a very small amount of expression of unknown etiology at an extremely low level (less than 0.1% preferably lees than 0.01%), for instance due to "leakage" or to random mutations within the genetic material of the expression host, is not excluded.

Finally, although the invention is explicitly not limited thereto, it should be noted that, especially when heterologous genes or mutant genes are expressed under the control of the promoters of the invention, the expression products thus obtained (optionally after post-translational modification) will in general not, or not to any significant extend, be able to induce the promoter.

In the invention use was made of various isogenic nisin-producing and non-producing derivatives of strain *L. lactis* MG1614 (Gasson, M. J. (1993) *J. Bacteriol.* 154, 1–9).

A transconjugent was obtained which possesses the nisin/sucrose transposon Tn5276; this strain has been named *L. lactis* NZ9700. Strain *L. lactis* NZ9800 was obtained by replacement of the nisA gene by a truncated ΔnisA gene, which contains a 4 bp deletion in position 284–287 (Kuipers et al., 1993). This strain is no longer capable of nisin production. Expression plasmids, such as pNZ9010 and pNZ9013 which possess, respectively, the nisA and the nisZ gene under the control of the efficient lac promoter from the lactose operon of *L. lactis* restore the capacity for nisin A and, respectively, Z production when they are introduced into strain NZ9800 (Kuipers et al., loc cit).

Transcription analyses of the nisA gene in various strains, such as NZ9700 and NZ9800, were carried out as previously described (Kuipere et al., loc cit) with the aid of a radio actively labelled nisA probe. Northern blotting of *L. lactis* NZ9700 RNA revealed a clear transcript of approximately 260 nucleotides (nt), whilst this was completely absent in the case of the RNA from strain Nz9800. However, when, as is described here in the invention, an amount of nisin (of between 0.01 and 1 $\mu$g/ml) was present in the culture medium of strain NZ9800, a clear transcript of the ΔnisA gene was detected. The ΔnisA gene itself can never yield an active nisin molecule by the above-mentioned frame-shift mutation. Subsequent studies demonstrated that other substances were also able to produce this transcription activation. These substance include, inter alia, the completely modified precursor nisin A, and the species subtilin leader nisin Z and S5T nisin Z obtained by protein engineering techniques which have been described previously. The latter mutant contains a dehydrobutyrine in position 5. An unmodified synthetic nisin A precursor was found to be incapable of transcription activation. Other antimicrobial peptides, such as lacticin 481, subtilin, pediocin PA-1 and lactococcin A were also incapable of transcription activation. This suggests that the modified structures in the nisin molecule play a role in the inducing capacity of nisin. Disruptions of the genes nisB and nisC, which are probably involved in the modification reactions in strain NZ9700, also resulted in inability to produce nisin A, although an intact nisA gene is present. In this case as well it was not possible to detect any nisA transcript at all. However, the transcription was able to take place again when a small amount of nisin was added to the medium. In subsequent studies it was demonstrated with the aid of transcriptional fusions between the nisA promoter fragment and the gusA gene from E. coli, coding for β-glucuronidase, with its inherent ribosome binding site in NZ9800, that β-glucuronidase activity was detectable only when nisin (or analogues thereof, such as S3T nisin Z, S5T nisin Z or T2S nisin Z and subtilin leader nisin Z) was introduced into the medium. The mutant T2S nisin Z, which was found to possess a Dha residue in position 2, surprisingly had both a higher activity towards various indicator organisms and better inducing characteristics than nisin A and nisin Z. The degree of gusA expression was found to depend on the amount of nisin used; higher expression was found with 0.028 µg/ml than with 0.014 µg/ml. It has thus been irrefutably demonstrated that it is possible, using the nisin promoter fragment, to bring a heterologous gene to expression under strict regulation, Consequently, it also demonstrated that it is possible to determine the nisin concentration with the aid of a reporter gene (for example the gusA gene), and such methods constitute a further aspect of the invention.

By cloning a fragment of ΦUS3 of L. lactis which has been demonstrated to be able to produce lysis, under the control of the nisA promoter fragment, it was also possible to achieve lysis of at least some of the cells after induction by nisin and it was possible to demonstrate that an appreciable amount of intracellular enzymes, such as, for example, aminopeptidese N (PepN) was liberated.

L. lactis strains of this type which show induced lysis can be very useful in acceleration of the development of taste in fermented dairy products or have industrial applications in the extraction of intracellular proteins or enzymes from L. lactis.

It is assumed that the autoregulation mechanism described also plays a role in the production of other antimicrobial peptides by lactic acid bacteria. In these cases, in a manner analogous to that described here for the nis promoter/nisin induction system, a regulated expression system can be developed with the relevant antimicrobial peptide (or analogues thereof) as inducer, and the promoter fragment of the structural gene as the element on which the regulation takes place. The expression strain used can then be the strain producing the antimicrobial peptide, in which the structural gene is switched off using methods which in themselves are well known (Leenhoute et al., and Kuipers et al., loc cit.). A plasmid with the relevant promoter fragment and gene(s) of interest can then be introduced into this lactic acid bacterium in the customary manner.

Furthermore, it is assumed that many other gene clusters exist in lactic acid bacteria which show similarities with the nisin gene cluster. In any case, homologous genes for nisABTCPRK have been found in the gene clusters of a few other lantibiotics, such as epidermin from Staphylococcus epidermidis, subtilin from Bacillus subtilis and pep5 from Staphylococcus epidermidis, which suggests a corresponding function.

Systems of this type can be used in the present invention.

In a particularly preferred aspect, the invention finally relates to a method for the extracellular production of proteins, in which method one or more genes which code for holines are brought to expression, in addition to the one or more genes which code for the protein(s) to be produced. Surprisingly, it has been found that these holines produce an increase in the secretion of these intracellular proteins, but without the cell undergoing complete lysis, in the case of the expression of the lytic genes described above.

This has the advantage that extracellular release of the proteins produced is obtained, if appropriate after prior intrucellular modifications, possibly without the cellular production mechanism for the proteins being completely lost, so that more efficient production can be achieved, in particular in continuous and/or overproduction.

This type of use of holine genes on their own—that is to say without lysine genes—has not yet been described in the prior art.

Without being restricted to any particular explanation, it is assumed that the holines increase the permeability of the cell envelope for the proteins produced by intracellular means.

Although this aspect of the method can also be used with promoters other than the promoters according to the application, it is particularly to be preferred to use the holine genes with an expression system according to the invention, so that the advantages described above are obtained.

The preferred embodiments of this system are the same as those indicated above.

Finally, the invention offers the possibility of determining the nisin concentration in a simple manner by using lactic acid bacteria in which the nisA promoter fragment is coupled to a promoterless reporter gene, such as the gusA gene of E. coil.

The invention will now be described with the aid of the following figures and non-limiting examples.

BRIEF DESCRIPTION OF THE DRAWINGS

The figures show:

FIG. 2. Northern blots of RNA from various L. lactis strains induced by nisin A and non-induced L. lactis strains, all probed with nisA.

FIG. 3. Northern blots of RNA from various L. lactis strains induced by nisin mutants or other bacteriocines and non-induced L. lactis strains, all probed with nisA.

FIGS. 4a–4b. Restriction map of the fragment from Tn5276 containing nisA promoter.

EXAMPLE 1

Transcription studies on ΔnisA of L. lactis NZ9800 with and without inducing agents With the aid of Northern blotting with a radioactively labelled nisA probe, it has been demonstrated that no transcription of ΔnisA takes place in strain NZ9800. Transcription does take place by complementing ΔnisA by nisA or nisZ on pNZ9010 and pNZ9013, respectively. Here it is now first demonstrated that in strain NZ9800 transcription activation takes place by the addition of a specific amount of nisin A.

The results of Northern blots of RNA of L. lactis strains NZ9700 and NZ9800 cultured with and without the presence of a specific amount of nisin A are shown in FIG. 2. It can clearly be seen from this figure that the transcript of the ΔnisA gone can be demonstrated in NZ9800 only when this strain is cultured in the presence of nisin A (0.01 to 1 μg/ml) in the medium. The conditions for these experiments were identical to those described in Kuipers at al., loc cit. and incorporated herein by reference. Subsequent studies demonstrated that substances already known per se from the prior art, i.e. nisin Z, completely modified precursor nisin A, subtilin leader nisin Z, A-4D precursor nisin Z and S5T nisin Z, were able to produce induction, although in the majority of cases the peptide concentration required to obtain induction of transcription was appreciably higher than that with nisin A or Z (FIG. 3).

Cell cultures which contain other bacteriocins, such as subtilin, lacticin 481 and lactococcin A, were not capable of producing detectable transcription activation, and the same was true of a synsthetically completely unmodified nisin precursor peptide (FIG. 3). It can clearly be seen from these results that only molecules which contain a modified (mutant) nisin fraction are capable of transcription activation of ΔnisA.

EXAMPLE 2

Controlled expression of gusA

Figure 1:
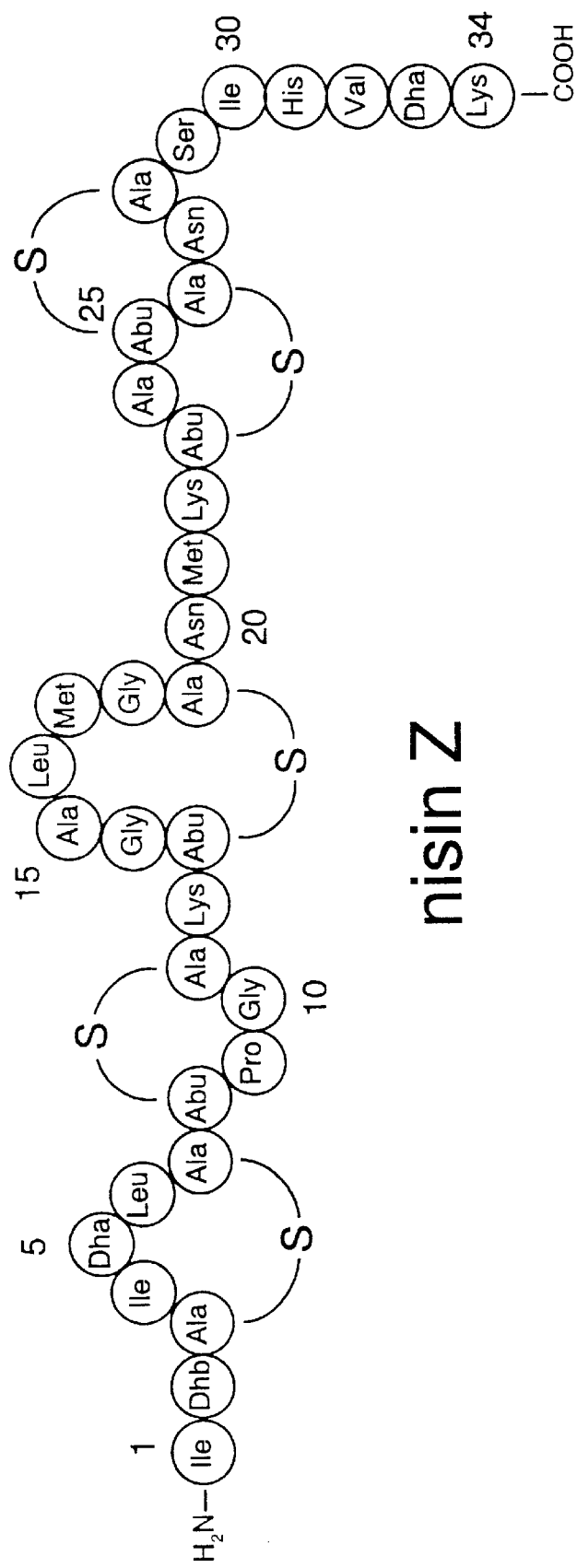
FIG. 1. Primary structure of nisin Z and the structures of the unsaturated amino acids dehydroalanine (Dha), dehydrobutyrine (Dhb), lanthionine (Ala-S-Ala) and β-methyllanthlonine (Abu-S-Ala).
Figure 5:
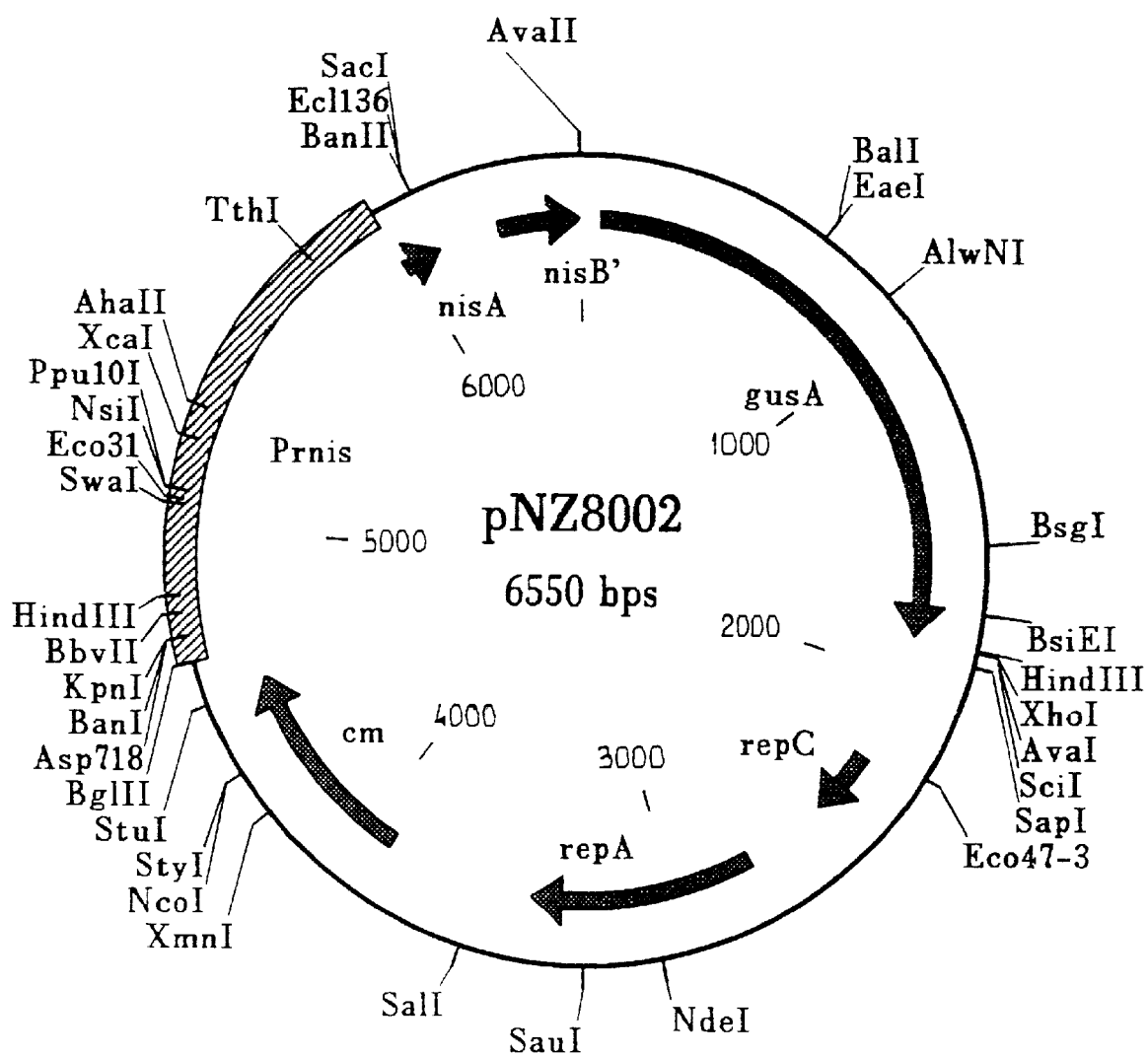
FIGS. 5–9. Restriction maps of constructs according to the invention, i.e. pNZ8002, pNZ8003, pNZ8008, pNZ8010, pNZ8011 and pNZ8013.
Figure 6:
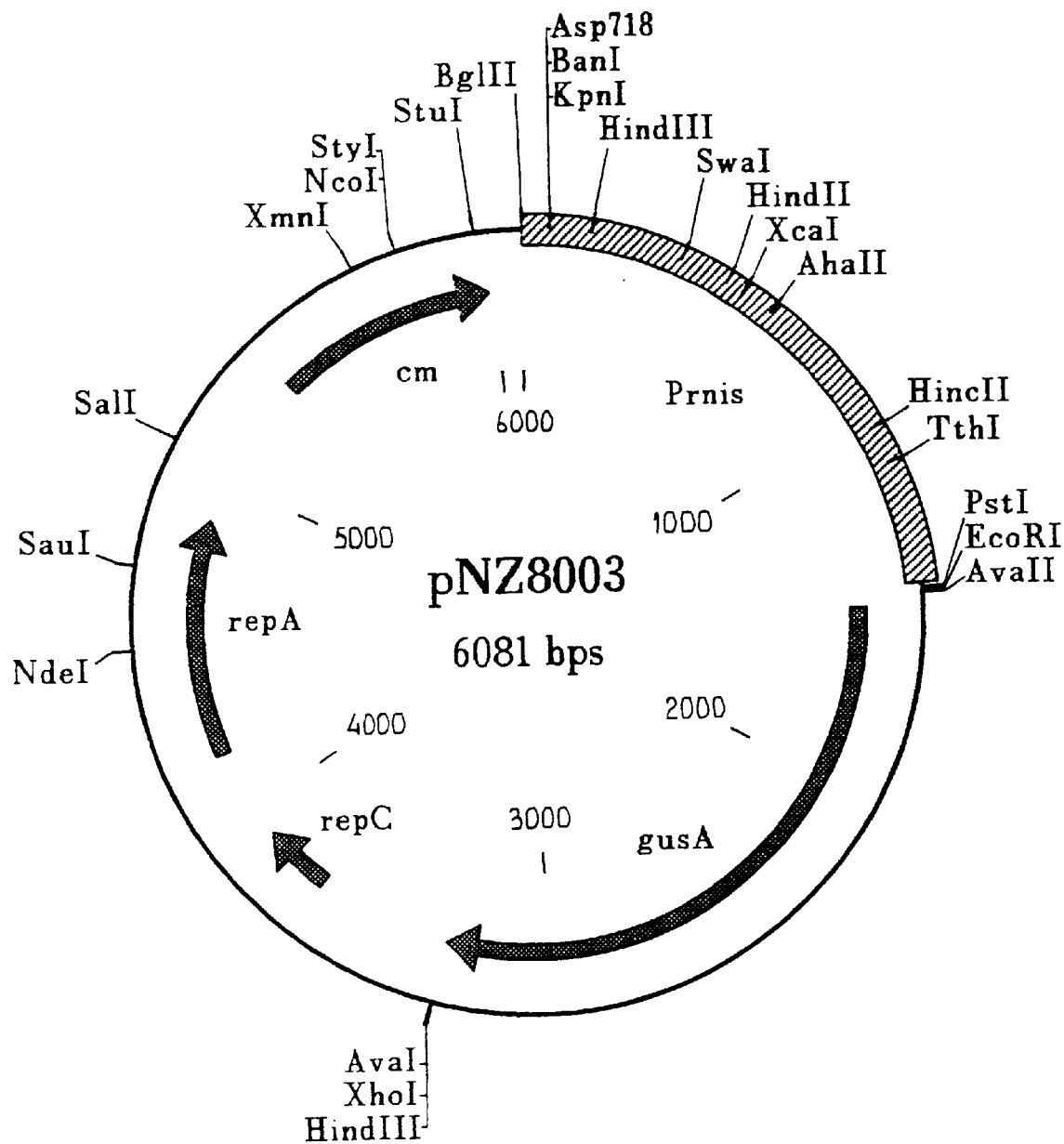
Figure 7:
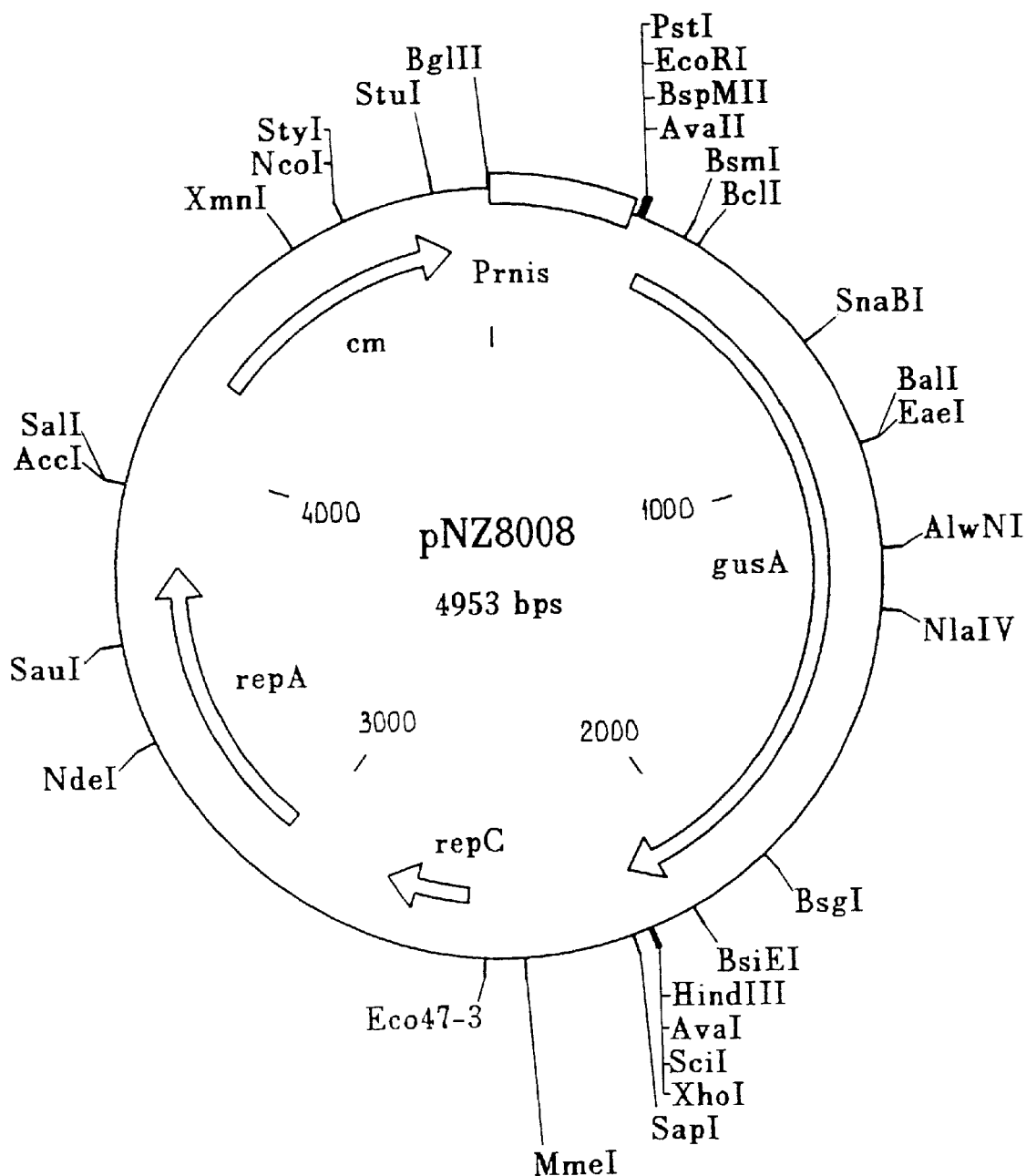
Figure 8:
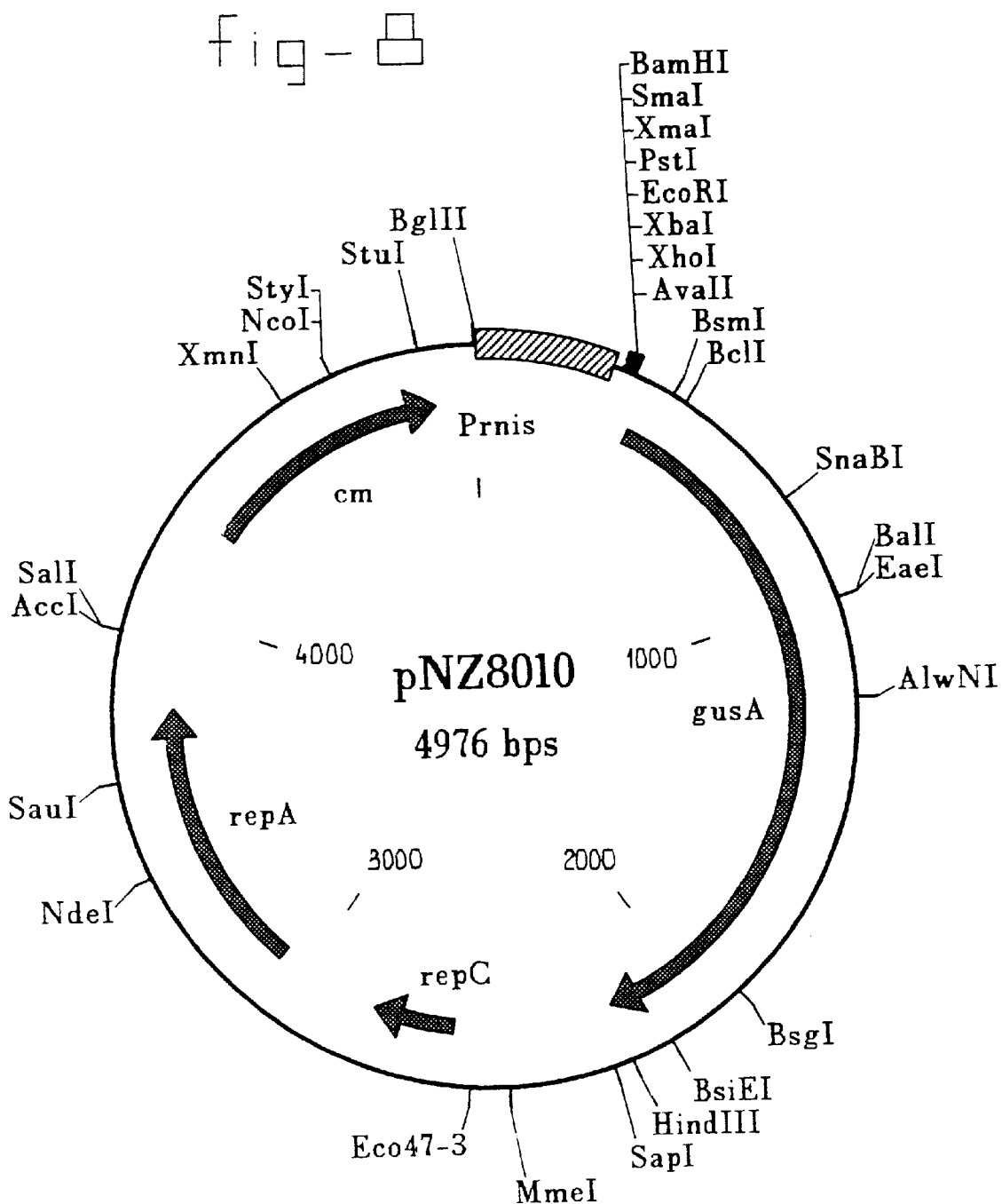
Figure 9:
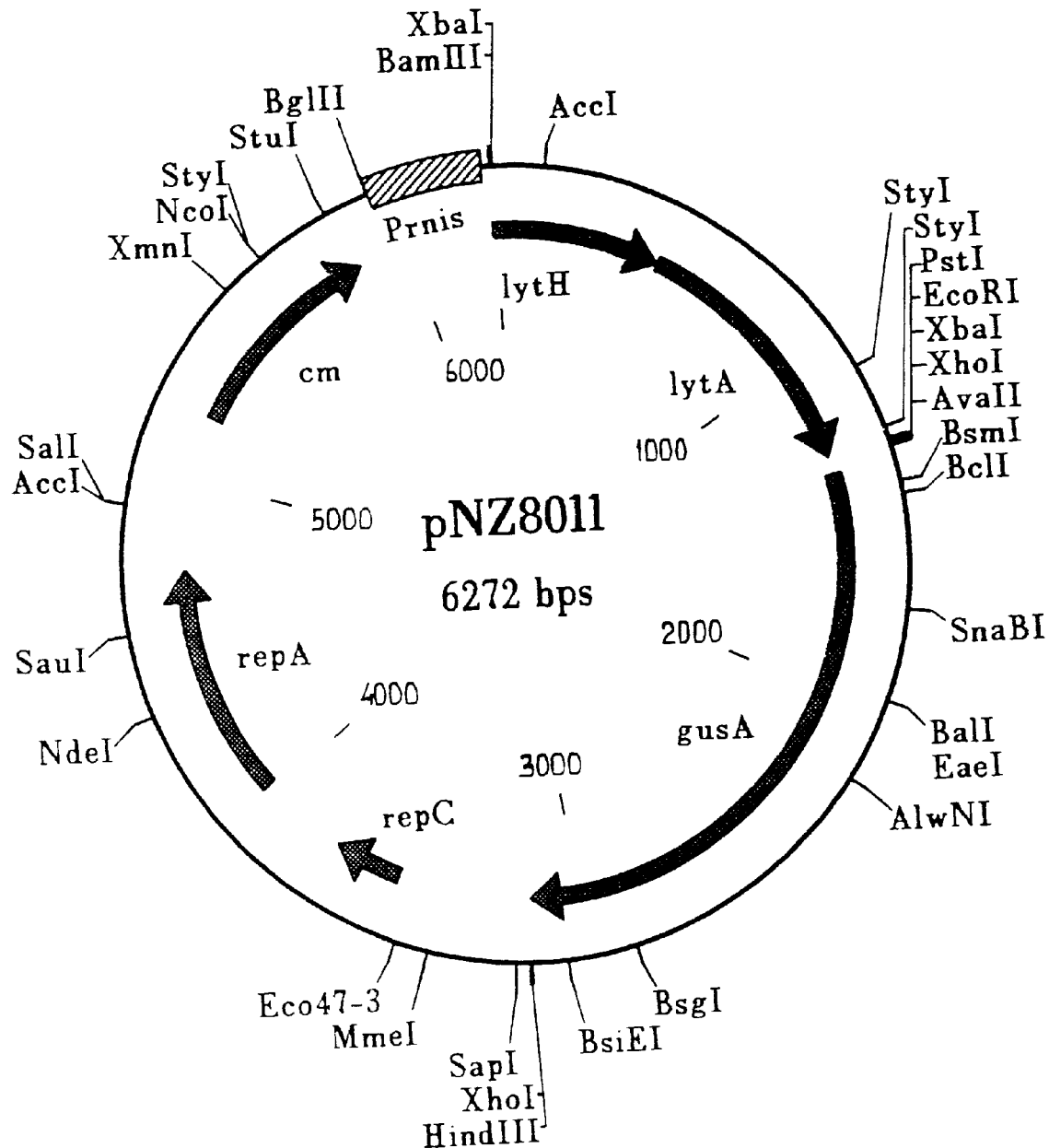

To demonstrate that genes other than nisA or ΔnisA can also be brought to controlled expression with the aid of the nisin promoter fragment, transcriptional fusions were made between fragments which contain the nisA promoter an a promoterless gusA gene. To this end, the large nisin promoter fragment, (BglII-Ecl1326II: 1444 bp, FIG. 4) was first cloned on the plasmid pNZ273, which contained the gusA gene and a polylinker sequence just upstream of the ribosome binding site, specifically in the BglII-ScaI (blunted) digested vector. This construct was named pNZ8003 (FIG. 5). In order to shorten the promoter fragment, the BglII-TthlIII fragment (FIG. 4) was then removed, the sticky ends were blunted with the aid of the Klenow fragment Of DNA polymerase I and an autoligation was carried out. The plasmid (pNZ8008, FIG. 5) thus obtained was introduced into L. lactis Nz9800 by means of electroporation and it was demonstrated that no β-glucuronidase activity was obtained on culture of the transformant in the absence of an inducing agent. However, by means of induction with extra-cellularly added nisin A or nisin Z in concentrations varying from 0.0001 to 0.1 μg/ml it was possible to obtain appreciable β-glucuronidase activity; see Table 1.

TABLE 1

β-glucoronidase activity of L. lactis NZ9800 with pNZ8008 after induction with various amounts of nisin A

| Induction amount of nisin A (μg/ml) | β-glucoronidase activity in cell-free extract (arbitrary units) |
|---|---|
| 0 | <0.1 |
| 0.0001 | 3 |
| 0.0005 | 18 |
| 0.0007 | 45 |
| 0.0070 | 90 |

It was also demonstrated that the purified mutants S3T nisin Z (contains a β-methyllanthionine instead of a lanthionine between residues 3 and 7) and T2S nisin Z (contains a Dha instead of a Dhb in position 2) gave clear βglucuronidase activity, whilst more of the first inducer (S3T) and less of the second inducer (T2S) was required in order to obtain the same β-glucuronidase activity as obtained with wild-type nisin (Table 1). This demonstrates that T2S nisin Z is a better inducer than the two wild-type nisins and also demonstrates that the type of nisin and nisin concentration in the medium also have an influence on the ultimate expression level. It was then demonstrated that no induction could be obtained with preparations containing subtilin or lactococcin A. After introduction of the same plasmid (pNZ8008) into NZ9700, a nisin A producer, constitutive β-glucuronidase production was found, which is to be expected because constitutive nisin A is also formed here. The gusA gene was also cloned approximately 300 bp downstream of nisA, in a vector preceded by the nis promoter, the ΔnisA fragment and part of the nisB gene (pNZ8002, FIG. 5). With a comparable amount of inducer, in NZ9800 this construct gave a βglucuronidose activity which was substantially lower (>20x) than that of pNZ8008, which indicates transcription attenuation, probably caused by the presence of an 'inverted repeat' sequence, located just upstream of the translation start of nisB. This reduced transcription level can be used to bring to expression genes for which it is considered desirable to restrict the maximum transcription level.

EXAMPLE 3

Controlled lysis of lactia acid bacteria

A vector with which lysis of *L. lactis* NZ9800 could be achieved in a controlled manner has been developer for the possible application of the system described above. To this end, a cassette was cloned in plasmid pNZ8010 (a derivative of PNZ8008 with a multiple cloning site for the gusA gene; FIG. 5), which cassette contains the genes ORF2 and lytA from *L. lactis* phage ΦUS3 (Platteeuw, C. and de Vos, W. M. (1992) Gene 118, 115–120. This construct was named pNZ8011 (FIG. 5). The ORF2 and lytA genes code for proteins which are, respectively, a presumed holine and a presumed emidase. The lytic effect after expression of these genes in *E. coli*. or *L. lactis* is already known. The plasmid pNZS8011 was introduced into strain *L. lactis* NZ9800 and these transformants were analysed during growth in the absence or the presence of nisin A. In the absence of nisin A normal growth took place, but in the presence of nisin A the optical density of the culture decreased sharply after about 30 min, which indicates inhibition of growth and lysis of the cells. Counts of surviving cells 2, 3 or 4 hours after induction (0.014 μg nisin A/ml) showed a reduction in viable cells by a factor of $10^3$ compared with the situation without induction (Table 2).

TABLE 2

Survival of cells which are capable of bringing lytic genes to expression under the influence of nisin induction
Number of survivors (100%) varies from $4*10^5 = 4*10^9$ (pNZ8008), $2*10^6 = 9.7*10^8$ (pNZ8011)
Colony-forming units *L. lactis* NZ9800

| Nisin A μg/ml | pNZ8008 | pNZ8011 |
|---|---|---|
| 0 | 100 | 100 |
| $7*10^{-4}$ | 100 | 0.1 |

In a subsequent experiment it was demonstrated that when the aminopeptidase N (PepN) was overproduced at the same time in this strain by the introduction of plasmid pNZ1120 (van Alen Boerrigter, L. J., Baankreis, R. and de Vos, W. M. (1991) *Appl. Environm. Microbio.* 265, 18499–18503), an intracellular accumulation of PepN was detected in the non-induced state without detectable PepN activity in the medium, whilst in the induced state (0.028 μg nisin A/ml) more than 60% of the total aminopeptidase N (PepN) formed was found in the supernatant of the culture after 6 hours (Table 3).

The abovementioned example reveals the great advantage of this system: without making major changes to the medium, the cells can be brought to lysis, or at least to the release of intracellular enzymes into the medium, using low nisin concentrations, which is of great importance for a number of (dairy) applications.

Surprisingly, a plasmid on which only ORF2 (assumed holine) was under the control of the nis promoter (pNZ8013) also led to a high percentage of secreted PepN (Table 3), after transformation of said plasmid to strain NZ9800 which contained pNZ1120 (PepN). This indicates that a holine an its own is already capable of secretion of relatively large amounts of a relatively large intracellular enzyme such as PepN (95 kDa).

This could have the advantage that the cells remain metabolically active for a longer period and, consequently, could be able to continue to produce more enzyme than is the case with total lysis.

TABLE 3

PepN activity in the cell-free extract (cfe) and in the supernatant (sup) of NZ9800 + pNZ1120 (pepN) + pNZ8011 (ORF2-lytA) or pNZ8013 (ORF2) with and without induction by nisin A

| Time (h) after induction | Induction (μg/ml nisA) | cfe (%) | sup (%) |
|---|---|---|---|
| pNZ8011 | | | |
| 2 | 0.03 | 85 | 15 |
|   | 0 | >98 | <2.0 |
| 3 | 0.03 | 87 | 13 |
|   | 0 | >98 | <2.0 |
| 4 | 0.03 | 85 | 15 |
|   | 0 | >98 | <2.0 |
| 5 | 0.03 | 78 | 22 |
|   | 0 | >98 | <2.0 |
| 6 | 0.03 | 38 | 62 |
|   | 0 | >98 | <2.0 |
| pNZ8013 | | | |
| 2 | 0.03 | 81 | 19 |
|   | 0 | >98 | <2.0 |
| 3 | 0.03 | 74 | 26 |
|   | 0 | >98 | <2.0 |
| 4 | 0.03 | 65 | 35 |
|   | 0 | >98 | <2.0 |
| 5 | 0.03 | 48 | 52 |
|   | 0 | >98 | <2.0 |
| 6 | 0.03 | 34 | 66 |
|   | 0 | >98 | <2.0 |

EXAMPLE 4

Overexpression of pepN in *L. lactis* NZ3900

Figure 10:
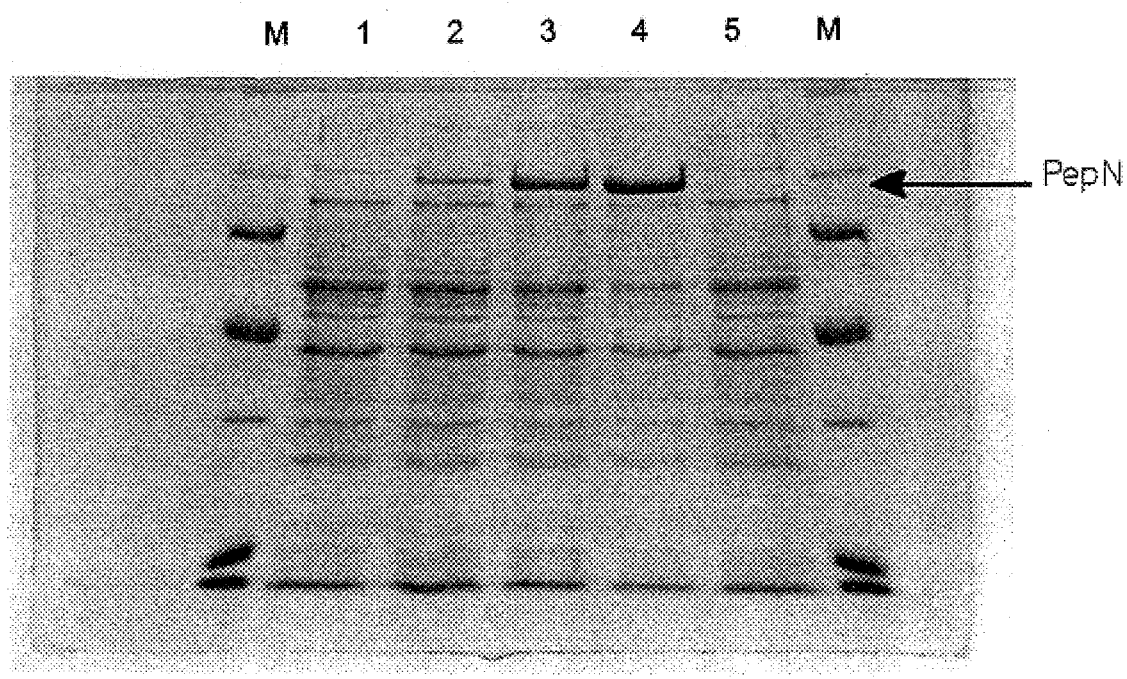
FIG. 10. Coomaassie blue stained gel of extracts of strain NZ 3900 containing pNZ 8040 producing Pep N. Lanes: 1 and 5, uninduced cells; Z, induced with 0,05 μg/l nisin A: 3, induced with 0,1 μg/l nisin A: 4, induced with 0.5 μg/l nisin A; M, the molecular weight marker.
Figure 11:
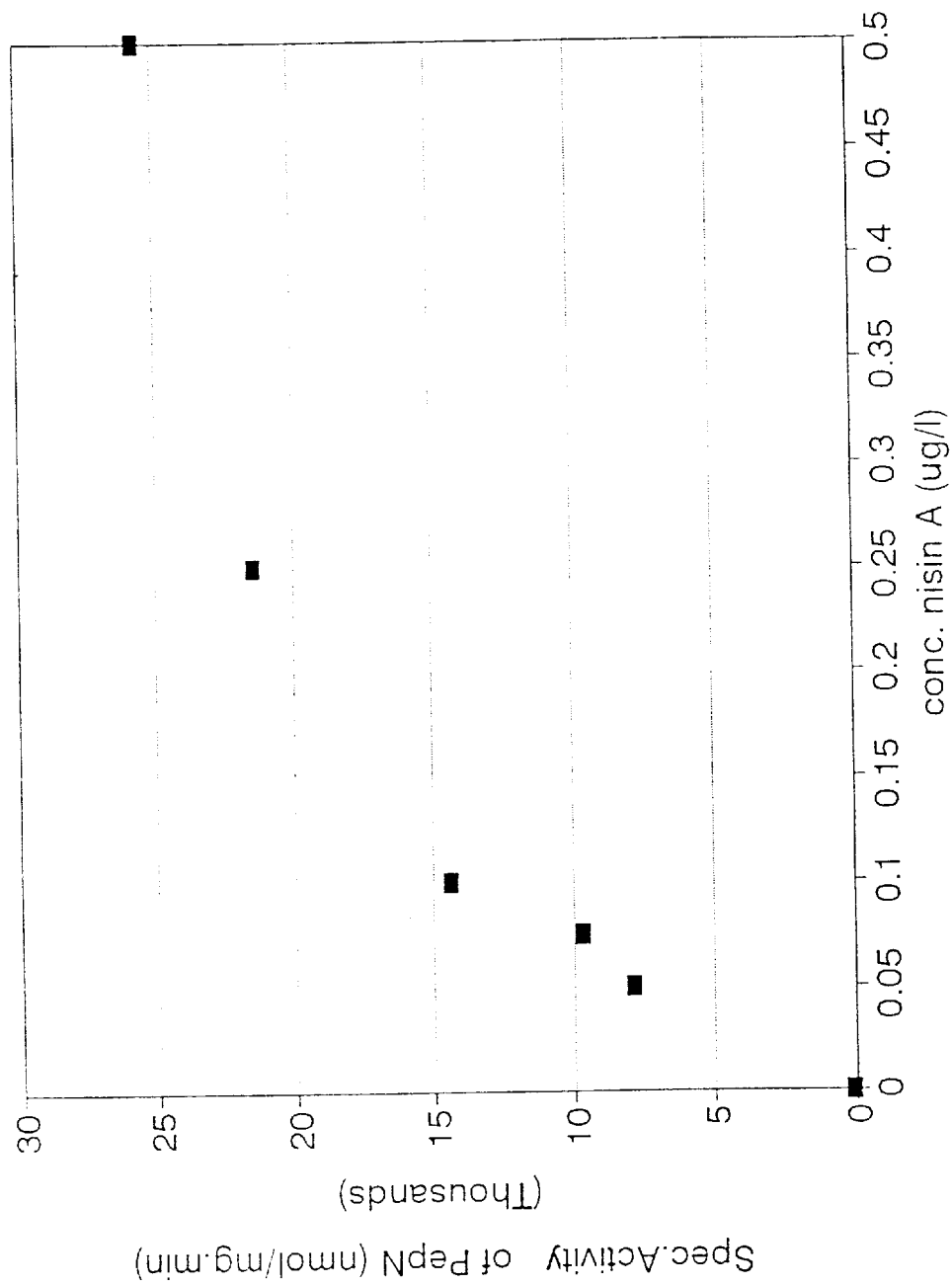
FIG. 11. The specific aminopeptidase N activity in nmol/mg·min in strain L. lactis Nz3900 containing pNZ8040 in the absence of nisin A and in the presence of various inducing concentrations of nisin A.
Figure 12:
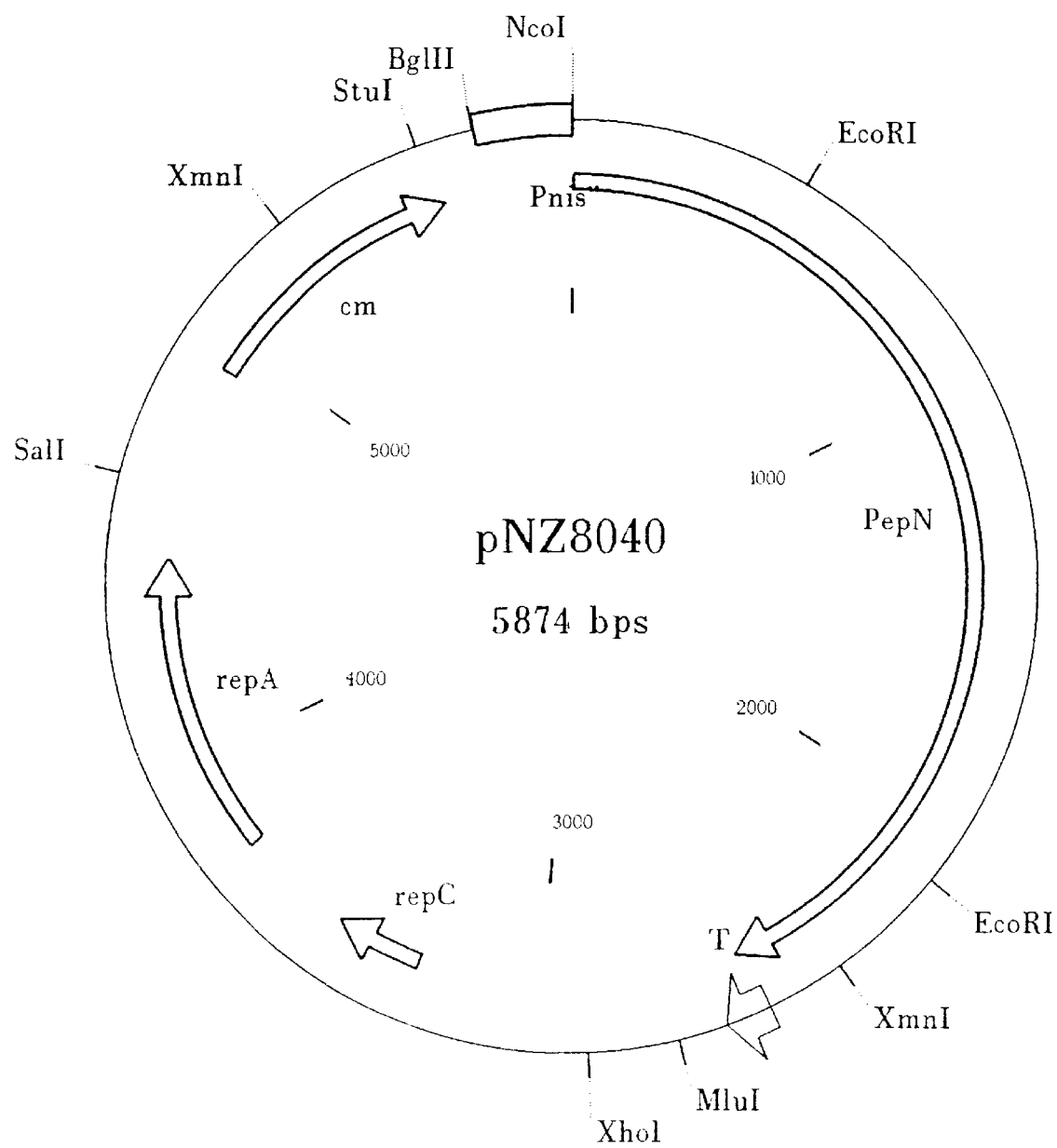
FIG. 12. Plasmid pNZ8040 containing the nisin promoter fused to the pepN gene
Figure 13:
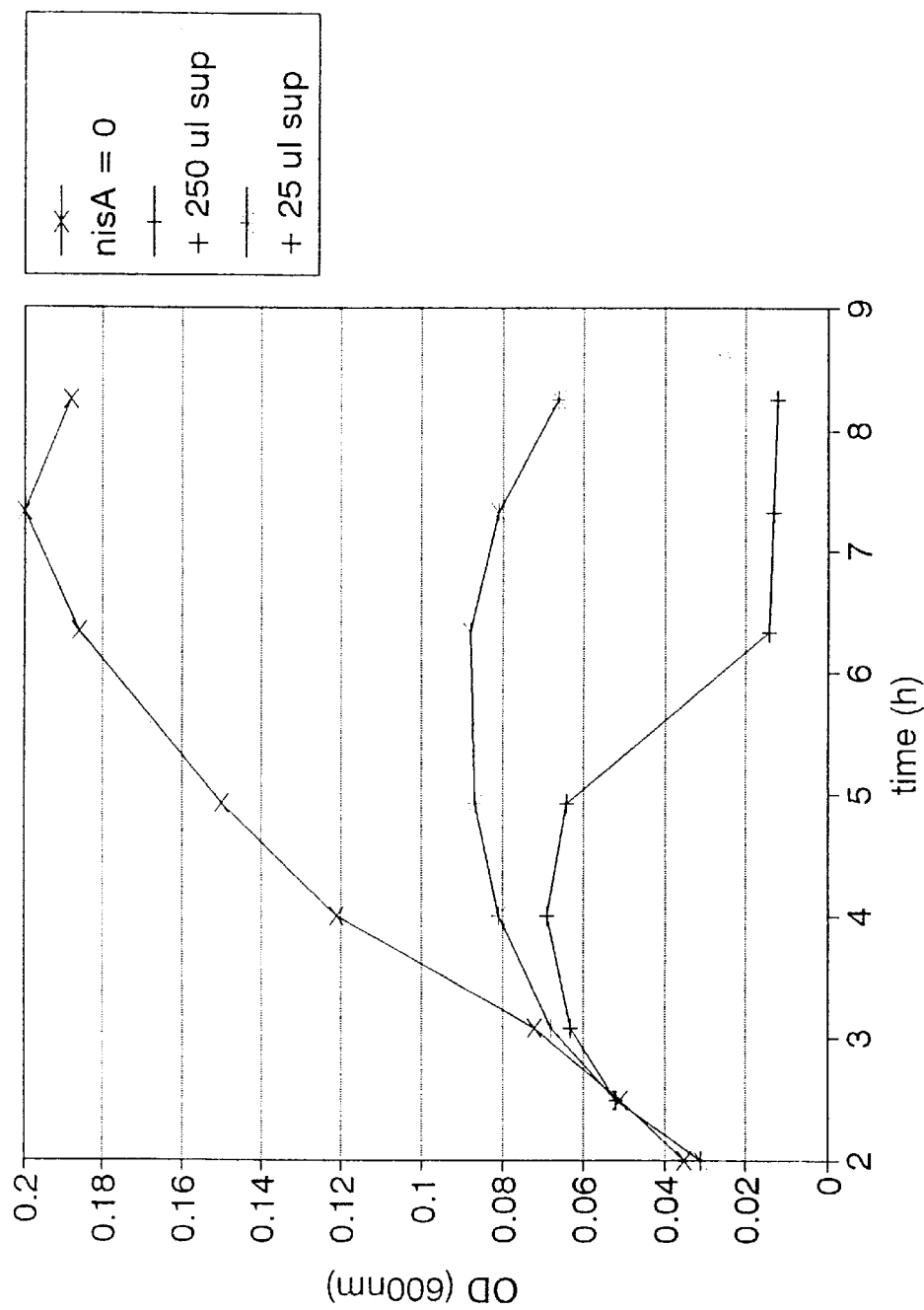
FIG. 13. Growth of L. lactis NZ9800 containing pNZ8011 in time, in the absence of a nisin producing culture supernatant and in the presence of nisin containing supernatant of strain NIZO R5.

The controlled expression of aminopeptidase N of *L. lactis* in *L. lactis* NZ3900 is an example of a significant overproduction of a homologous protein in *L. lactis*. This overproduction allows rapid extraction and purification of great amounts of PapN that can be used in biochemical studies. This might be useful to assess the specific contribution of this aminopeptidase N in debittering activity after the proteolytic degradation of casein in milk and for direct application of this strain in dairy fermentations. The pepN gene was cloned as a 2.4-kb PCR-fragment derived from pNZ1120 (Alen-Boerrigter van, I. J., R. Baankreis and W. M. de Vos. 1991. Appl. Environ. Microbiol. 57:2555–2561.) as a template, behind the nisA promoter, generating pNZ8040. The primer sequences used were 5'GCAACTG-CAGGAGAAGCCATGGCTGTAAAACG 3' (SEQ ID NO: 1) and 5'CCTTATTCTCGAGTTGATTGTTCTATCG 3' (SEQ ID NO. 2). This plasmid was introduced in strain NZ3900 (an MG1363 derivative containing the nisR and nisK genes integrated in the pepN locus on the chromosome). This strain containing pNZ8040 was grown until an $OD_{600}$ of 0.5 was reached and then devided in 25 ml tubes. Three tubes were induced with $5.10^{-4}$, $1.10^{-4}$, $5.10^{-5}$ μg/ml nisin A, respectively, and one tube was incubated without induction. After 90 minutes growth at 30°C., cells were harvested and cell free extracts were prepared. 100 μl of the extracts were mixed with equal amounts of sample buffer and 20 μl was applied to a 10% polyacrylamide-SDS gel. FIG. 10 shows the overproduction of the 95-kDa aminopeptidase N after induction (lane 2,3,4). This result indicates that a major portion of intracellular protein is formed by the overproduced PepN protein. The cell free extracts were also used in an activity assay. PepN activity was determined at 30° C. by monitoring the hydrolysis of the substrate lysyl-p-nitroanilide as described before (Exterkate, F. J. 1984. Appl. Environ. Microbiol. 47,.177–183). Protein concentrations were determined as described previously (Bradford, M. M. 1976. Anal. Biochem. 72:248–354). FIG. 11 shows the specific activity in nmol/mg·min. of aminopeptidase N after induction with various concentrations of nisin A. This dose-response curve shows the high production of the desired protein by induction with nisin A. A specific PepN activity of 25000 nmol/mg·min was achieved using 0.5 µg/l nisin A as an inducer, a level that has never been reached before by use of other (constitutive) promoters. This is at least a 400 fold overproduction compared to the production level of the chromosomal encoded pepN.

EXAMPLE 5

Controlled lysis of *L. lactis* in milk

This example shows the possibility to produce lytic (lethal) enzymes by expressing genes under control of the nisA promoter by *L. lactis* in a dairy environment. Strain *L. lactis* Nz9800 (ΔnisA. lac-, prt-) containing the plasmid pNZ8011 (lyth-lytA cloned behind the nisA promoter) was grown in milk containing 0.5% casiton, 0.5% glucose and 10 µg/ml chloramphenicol. As a control strain *L. lactis* NZ9800 containing pNZ8008 (nisA promoter fused to the gusA gene) was used. While growing the strains in milk, the $OD_{600}$ of samples were measured after clearing 100 µl milk sample culture with 900 µl 0.5M Sodium-borate/10 mM EDTA. At an $OD_{600}$ of 0.05 the cultures were devided in different tubes and supernatant of the wild-type nisin producing strain *L. lactis* NIZO R5 (Galesloot, T. E., and J. W. Pette. 1957. Neth. Milk Dairy J. 11:144–151) was added. Strain NIZO R5 was also grown in milk. The pH of this overnight culture was adjusted to 6.5 by use of 1M NaOH. Sodium citrate (2 ml) was added to clear the milk and after clearing for 15 minutes on ice the cells were centrifuged for 30 minutes. The supernatant was used for induction. 250 µl and 25 µl of supernatant was added to 25 ml of NZ9800 cultures. After induction by NIZO R5 supernatant the growth of the strains was measured and after 2 hours the NZ9800+pNZ8011 cells started to lyse. This lysis was caused by expression of the lytH, encoding the holin, and the lytA gene, encoding an amidase, while the NZ9800 containing pNZ8008 strain was not lysed. This experiment clearly demonstrates the feasibility of controlled lysis of a dairy starter strain by us of a simple fermented, food grade product i.e. a nisin producing *L. lactis* grown in milk.

We claim:

1. A method for the controlled expression of a gene, comprising the steps of;
   a. providing;
      i. a DNA fragment comprising a gene or genes under transcriptional control of a promoter, wherein the promoter is obtained from a Gram-positive microbial gene coding for a lantibiotic precursor in a gene cluster for synthesis of a lantibiotic and the promoter is inducible by the lantibiotic which is a product of the gene cluster;
      ii. a Gram-positive expression host having a Gram-positive two-component regulatory system for transcriptional activation of the promoter by addition of the lantibiotic inducer, wherein the two-component regulatory system corresponds to a sensor and a response regulator which are products of the gene cluster; and
      iii. a lantibiotic inducer, or a mutant or derivative thereof, for transcriptionally activating the promoter;
   b. inserting the DNA fragment into the Gram-positive expression host;
   c. inducing expression of the gene or genes via the two-component regulatory system by addition of the inducer.

2. A method for the controlled expression of a gene as claimed in claim 1, wherein the two products of the two-component regulatory system are naturally expressed by the Gram-positive expression host.

3. A method for the controlled expression of a gene as claimed in claim 1, wherein the Gram-positive expression host is stably transformed with a DNA fragment comprising at least one gene for expressing the two products of the two-component regulatory system.

4. The method according to claim 1, wherein the promoter is the promoter of the nisA gene from *Lactococcus lactis*.

5. The method according to claim 1, wherein the inducer is acceptable for food products.

6. The method according to claim 1, wherein the inducer is produced by a lactic acid bacterium.

7. The method according to claim 1, wherein the inducer is chosen from nisin A, nisin Z and mutants or derivatives thereof.

8. The method according to claim 1, wherein the inducer is added as a culture of a lactic acid bacterium.

9. The method according to claim 1, wherein the inducer is added at a concentration of 0.00001–10 mg/l.

10. The method according to claim 1, wherein the DNA fragment comprising the gene or genes is operably linked to a DNA fragment containing the promoter.

11. The method according to claim 1, wherein the DNA fragment comprises a gene coding for one of a holine and a lytic enzyme and expression of the DNA fragment results in lysis of the microorganism or the release of intracellular proteins into the medium.

12. The method according to claim 1, wherein the Gram-positive expression host is a strain of *Lactococcus lactis*.

13. A lactic acid bacterium, comprising:
   a. a DNA fragment comprising a gene or genes under transcriptional control of a promoter, wherein the promoter is obtained from a Gram-positive microbial gene coding for a lantibiotic precursor in a gene cluster for synthesis of a lantibiotic and the promoter is inducible by a lantibiotic inducer which is a product of the Gram-positive microbial gene cluster, wherein said DNA fragment is exogenous to said lactic acid bacterium; and
   b. a Gram-positive two-component regulatory system capable of transcriptional activation of the promoter by addition of the lantibiotic inducer, wherein the two-component regulatory system corresponds to a sensor and a response regulator which are products of the gene cluster.

14. Lactic acid bacterium according to claim 13, wherein the promoter is the NisA promoter of *L. lactis*.

15. Lactic acid bacterium according to claim 13 being a strain of *L. lactis*.

16. Lactic acid bacterium according to claim 13, wherein said gene or genes code for one of a holine and a lytic enzyme.

17. A method for determining the concentration of an inducer in a medium comprising:
   a. adding to said medium a bacterium according to claim 13;
   b. determining the degree of expression of said gene or genes; and
   c. correlating said degree of expression to the concentration of an inducer in the medium.

18. The method according to claim 17, wherein the promoter is the nisA promoter and the inducer is nisin or a mutant or a derivative thereof.

19. A vector, comprising a DNA fragment comprising a gene or genes under transcriptional control of a promoter, wherein the promoter is obtained from a Gram-positive microbial gene coding for a lantibiotic precursor in a gene cluster for synthesis of a lantibiotic and the promoter is inducible by a lantibiotic inducer which is a product of the Gram-positive microbial gene cluster and which transcriptionally activates the promoter via a Gram-positive two-component regulatory system, wherein the two-component regulatory system corresponds to a sensor and a response regulator which are products of the gene cluster.

20. vector according to claim 19, wherein the promoter is a NisA promoter of *L. lactis*.

21. The vector according to claim 19, being a plasmid.

22. The vector according to claim 19, wherein the DNA fragment comprises a gene or genes coding for one of a holine and a lytic enzyme.

* * * * *

UNITED STATES PATENT AND TRADEMARK OFFICE
CERTIFICATE OF CORRECTION

PATENT NO. : 5,914,248
DATED : June 22, 1999
INVENTOR(S): Oscar Paul Kuipers et al.

It is certified that error appears in the above-identified patent and that said Letters Patent is hereby corrected as shown below:

Column 1 Line 6 "bacteriaum" should read --bacterium--.

Column 1 Line 13 "known Systems" should read --known systems--.

Column 1 Line 21 "in induced" should read --is induced--.

Column 1 Line 47 "Lakehmidevi" should read --Lakshmidevi--.

Column 1 Line 66 "Israeleen" should read --Israelsen--.

Column 2 Line 19 "operon" should read --operons--.

Column 2 Line 31 "galaotosidase" should read --galactosidase--.

Column 2 Line 64 "trancription" should read --transcription--.

Column 3 Line 5 "for sample" should read --for example--.

Column 3 Line 22 after "make it" delete --is--.

Column 3 Line 57 "to this and" should read --to this end--.

Column 4 Line 5 "more" should read --More--.

Column 4 Line 24 "it has ben" should read --it has been--.

Column 4 Line 25 "Strictly" should read --strictly--.

UNITED STATES PATENT AND TRADEMARK OFFICE
CERTIFICATE OF CORRECTION

PATENT NO. : 5,914,248  
DATED : June 22, 1999  
INVENTOR(S) : Oscar Paul Kuipers et al.

Page 2 of 6

It is certified that error appears in the above-identified patent and that said Letters Patent is hereby corrected as shown below:

Column 4 Line 36 "fragpent" should read --fragment--.

Column 4 Line 38 "paptide" should read --peptide--.

Column 4 Line 47 "lantibiotios" should read --lantibiotics--.

Column 5 Line 28 "use" should read --used--.

Column 5 Line 44 "in based" should read --is based--.

Column 5 Line 56 "micro-organims" should read --micro-organisms--.

Column 6 Line 3 "bacteia" should read --bacteria--.

Column 6 Line 3 "is" should read --are--.

Column 6 Line 37 "polycistronio" should read --polycistronic--.

Column 8 Line 19 "famillarity" should read --familiarity--.

Column 8 Line 20 "paptides" should read --peptides--.

Column 8 Line 38 "raferred" should read --referred--.

Column 8 Line 39 "olecular cloning" should read --molecular cloning--.

Column 9 Line 51 "gone" should read --gene--.

UNITED STATES PATENT AND TRADEMARK OFFICE
CERTIFICATE OF CORRECTION

PATENT NO. : 5,914,248
DATED : June 22, 1999
INVENTOR(S): Oscar Paul Kuipers et al.

It is certified that error appears in the above-identified patent and that said Letters Patent is hereby corrected as shown below:

Column 10 Lines 11-12 "haterologous" should read --heterologous--.

Column 10 Line 16 "On" should read --One--.

Column 10 Line 18 "Schimmeloultures" should read --Schimmelcultures--.

Column 10 Line 55 "as much" should read --as such--.

Column 11 Line 55 "nisa" should read --nisA--.

Column 12 Line 18 "logaritmic" should read --logarithmic--.

Column 12 Line 36 "extend" should read --extent--.

Column 12 Line 56 "Kuipere" should read --Kuipers--.

Column 12 Line 60 "Nz9800" should read --NZ9800--.

Column 13 Line 2 "These substance" should read --These substances--.

Column 13 Line 50 "aminopeptidese" should read --aminopeptidase--.

Column 14 Line 2 "Leenhoute" should read --Leenhouts--.

Column 14 Line 27 "intrucellular" should read --intracellular--.

Column 14 Line 60 "β-methyllanthlonine" should read --β-methyllanthionine--.

UNITED STATES PATENT AND TRADEMARK OFFICE
CERTIFICATE OF CORRECTION

PATENT NO. : 5,914,248
DATED : June 22, 1999
INVENTOR(S) : Oscar Paul Kuipers et al.

It is certified that error appears in the above-identified patent and that said Letters Patent is hereby corrected as shown below:

Column 15 Line 8 "Z" should read --2--.

Column 15 Line 12 "Nz3900" should read --NZ3900--.

Column 15 Line 41 "gone" should read --gene--.

Column 15 Line 57 "synsthetically" should read --synthetically--.

Column 16 Line 2 "promoter an" should read --promoter and--.

Column 16 Line 7 "Scal" should read --ScaI--.

Column 16 Line 11 "fragment Of" should read --fragment of--.

Column 16 Line 14 "Nz9800" should read --NZ9800--.

Column 16 Line 59 "βglucuronidose" should read --β-glucuronidase--.

Column 17 Line 2 "lactia" should read --lactic--.

Column 17 Line 5 "has been developer" should read --has been developed--.

Column 17 Line 11 after "115-120." insert right parenthesis --)--.

Column 17 Line 17 "pNZS8011" should read --pNZ8011-- (delete "S").

Column 17 Table 2, line 3 of header, delete equal sign (=) and insert hyphen (-).

UNITED STATES PATENT AND TRADEMARK OFFICE
CERTIFICATE OF CORRECTION

PATENT NO. : 5,914,248                  Page 5 of 6
DATED        : June 22, 1999
INVENTOR(S) : Oscar Paul Kuipers et al.

It is certified that error appears in the above-identified patent and that said Letters Patent is hereby corrected as shown below:

Column 17 Table 2, line 4 of header, delete equal sign (=) and insert hyphen (-).

Column 17 Table 2, line 5 of header, "2*10$^6$" should read --2*10$^8$--.

Column 17 Line 44 "L.J." should read --I.J.--.

Column 17 Lines 64-65 "an its own" should read --on its own--.

Column 18 Line 43 "PapN" should read --PepN--.

Column 18 Line 60 "devided" should read --divided--.

Column 19 Line 8 "47,.177" should read --47:177--.

Column 19 Line 30 "Nz9800" should read --NZ9800--.

Column 20 Line 1 "(lyth-lytA" should read --(lytH-lytA--.

Column 20 Line 8 "devided" should read --divided--.

Column 20 Line 27 "by us of" should read --by use of--.

Column 23 Line 2 Claim 1 after "gene" insert --or genes--.

Column 23 Line 3 Claim 1 after "comprising" delete ";" and insert --:--.

Column 23 Line 4 Claim 1 after "providing" delete semicolon.

UNITED STATES PATENT AND TRADEMARK OFFICE
CERTIFICATE OF CORRECTION

PATENT NO. : 5,914,248
DATED : June 22, 1999
INVENTOR(S) : Oscar Paul Kuipers et al.

It is certified that error appears in the above-identified patent and that said Letters Patent is hereby corrected as shown below:

Column 24 Line 20 Claim 14 "NisA" should read --nisA--.

Column 24 Line 52 Claim 20 "NisA" should read --nisA--.

Signed and Sealed this

First Day of August, 2000

Attest:

Q. TODD DICKINSON

Attesting Officer

Director of Patents and Trademarks

```
                         SEQUENCE LISTING (1) GENERAL INFORMATION:

(iii) NUMBER OF SEQUENCES:   4

(2) INFORMATION FOR SEQ ID NO: 1:

(i) SEQUENCE CHARACTERISTICS:
          (A) LENGTH:   32
          (B) TYPE:  NUCLEIC ACID
          (C) STRANDEDNESS:  SINGLE
          (D) TOPOLOGY:  UNKNOWN (xi) SEQUENCE DESCRIPTION: SEQ ID NO: 1:

GCAACTGCAG GAGAAGCCAT GGCTGTAAAA CG                                 32

(2) INFORMATION FOR SEQ ID NO: 2:

(i) SEQUENCE CHARACTERISTICS:
          (A) LENGTH:   28
          (B) TYPE:  NUCLEIC ACID
          (C) STRANDEDNESS:  SINGLE
          (D) TOPOLOGY:  UNKNOWN (xi) SEQUENCE DESCRIPTION: SEQ ID NO: 2:

CCTTATTCTC GAGTTGATTG TTCTATCG                                      28

(2) INFORMATION FOR SEQ ID NO: 3:

(i) SEQUENCE CHARACTERISTICS:
          (A) LENGTH:   34
          (B) TYPE:  AMINO ACID
          (C) STRANDEDNESS:  SINGLE
          (D) TOPOLOGY:  UNKNOWN
```

(xi) SEQUENCE DESCRIPTION: SEQ ID NO: 3:

Ile Xaa Ala Ile Xaa Leu Ala Xaa Pro Gly Ala Lys Xaa
                5                   10

Gly Ala Leu Met Gly Ala Asn Met Lys Xaa Ala Xaa Ala
     15              20                  25

Asn Ala Ser Ile His Val Xaa Lys
             30

(2) INFORMATION FOR SEQ ID NO: 4:

(i) SEQUENCE CHARACTERISTICS:
        (A) LENGTH: 1446
        (B) TYPE: NUCLEIC ACID
        (C) STRANDEDNESS: SINGLE
        (D) TOPOLOGY: UNKNOWN (xi) SEQUENCE DESCRIPTION: SEQ ID NO: 4:

```
AGATCTTTAA AGCAACACCT CCTAATAAAG TATGGCTGGG AGACATGACC         50

TATATCCCTA CCAAAGAAGG TACCTTATAC TTAGCCGTGA ATATCGACGT        100

TTTTTCACGT AAGATTGTAG GCTGGTCAAT GTCTTCACGG ATGCAAGATA        150

AACTGGTGAG GGATTACTTC TTACAAGCTT GTGGGAAAGA ACATCCTCAG        200

CCTGGCTTGA TTGTCCATAC TGATCAAGGG AGTCAATATA CAAGCTCTCG        250

TTATCAATCT ACTCTTCGTC AAGTCGGTGG TCAATCTAGC ATGAGTCGTA        300

AAGGAAATCC CTATGACAAT GCAATGATGG AGTCTTTTTA TAAGACGCTA        350

AAGAGGGAGC TTATTAATGA TGCTCATTTT GAGACAAGAG CTGAGGCTAC        400

TCAAGAAATA TTTAAATACA TTGAGACCTA TTACAATACA AAAAGGATGC        450

ATTCAGGTCT TGATTACAAG TCTCCAAAAG ACTTTGAAAA ATATAATTCT        500

TAAATTCTCT TAACTCCGTG TCTAGTTTTT CGTTGACTTT CCATTATGCT        550

TGGATTTTTT ATTGTTTAAT TCCCTTTTTT GTATACAAGC TCGTATTCTT        600

AACAAATAAT TGGCATATCG GGTTTAAAAA TACTATGTGT TTTAAAGAAT        650

CTCTCATGAG TTTGACGCCA ATAACTTAGA TTAAAATCAC CGTCACCTTA        700

TTTTTAGGCA CGTTCGGCAG TAACCTTATC AAAGGTATCT CGGTCATTAA        750

GTTTCATGAT AGTATTTACT ATTTTGACTG GTTTTTGTTA TTATCCAATC        800

GTTAAAATGA CAAAAACAAA TAGATAAATA GATAAATATT TATGGGGAGG        850

ACAAGTGAAC TTATCATGAT TAATTGTAAA CGATTGAGTT CTGAATGTTT        900

CAAATTATGA GGAACAACAG AGTTGGACTA TTCTTTAAAC GCCTCGACGA        950

TACCATCACT CTTCATTAGC CTAAAATTAA CAAGTTAAAA TCATTAGAAT       1000

AATCTCTTTT ACAAAAAATA TTTATTTAAG TTATAGTTGA CGAATATTTA       1050

ATAATTTTAT TAATATCTTG ATTTTCTAGT TCCTGAATAA TATAGAGATA       1100

GGTTTATTGA GTCTTAGACA TACTTGAATG ACCTAGTCTT ATAACTATAC       1150

TGACAATAGA AACATTAACA AATCTAAAAC AGTCTTAATT CTATCTTGAG       1200

AAAGTATTGG TAATAATATT ATTGTCGATA ACGCGAGCAT AATAAACGGC       1250

TCTGATTAAA TTCTGAAGTT TGTTAGATAC AATGATTTCG TTCGAAGGAA       1300

CTACAAAATA AATTATAAGG AGGCACTCAA AATGAGTACA AAAGATTTTA       1350

ACTTGGATTT GGTATCTGTT TCGAAGAAAG ATTCAGGTGC ATCACCACGC       1400

ATTACAAGTA TTTCGCTATG TACACCCCGT TGTAAAACAG GAGCTC          1446
```